(12) United States Patent
Schrader et al.

(10) Patent No.: US 9,505,796 B2
(45) Date of Patent: Nov. 29, 2016

(54) PHOSPHORYLATED A2A RECEPTOR AGONISTS

(71) Applicant: Crozet Medical GMBH, Dusseldorf (DE)

(72) Inventors: Jurgen Schrader, Dusseldorf (DE); Christa Muller, Bonn (DE); Ali El-Tayeb, Bonn (DE); Jamshed Iqbal, Bonn (DE)

(73) Assignee: Crozet Medical GmbH (DE)

( * ) Notice: Subject to any disclaimer, the term of this patent is extended or adjusted under 35 U.S.C. 154(b) by 0 days.

(21) Appl. No.: 14/108,010

(22) Filed: Dec. 16, 2013

(65) Prior Publication Data

US 2014/0288019 A1   Sep. 25, 2014

Related U.S. Application Data

(62) Division of application No. 12/293,983, filed as application No. PCT/EP2007/052716 on Mar. 21, 2007, now abandoned.

(60) Provisional application No. 60/819,400, filed on Jul. 10, 2006.

(30) Foreign Application Priority Data

Mar. 21, 2006 (EP) .................................. 06111493

(51) Int. Cl.
   *C07H 19/20* (2006.01)
(52) U.S. Cl.
   CPC ..................... *C07H 19/20* (2013.01)
(58) Field of Classification Search
   None
   See application file for complete search history.

(56) References Cited

U.S. PATENT DOCUMENTS

| | | | |
|---|---|---|---|
| 3,919,184 A | | 11/1975 | Furukawa et al. |
| 5,654,285 A | | 8/1997 | Ingall et al. |
| 5,877,180 A | * | 3/1999 | Linden et al. ............... 514/45 |
| 6,448,238 B1 | | 9/2002 | Shoichet et al. |
| 6,514,949 B1 | | 2/2003 | Linden et al. |
| 6,531,457 B2 | | 3/2003 | Linden et al. |
| 2005/0053612 A1 | * | 3/2005 | Granstein et al. ......... 424/184.1 |
| 2010/0048501 A1 | | 2/2010 | Schrader et al. |

FOREIGN PATENT DOCUMENTS

| | | | |
|---|---|---|---|
| BE | 801 135 A1 | 10/1973 | |
| BE | WO 2007020018 A1 * | 2/2007 | ........... A61K 31/513 |
| EP | 0 354 180 A2 | 2/1990 | |
| EP | 0 508 687 A1 | 10/1992 | |
| EP | 1 316 559 A1 | 6/2003 | |
| WO | WO 93/08206 A1 | 4/1993 | |
| WO | WO 93/23417 A1 | 11/1993 | |
| WO | WO 93/23418 A1 | 11/1993 | |
| WO | WO 95/30683 A1 | 11/1995 | |
| WO | WO 99/34804 A1 | 7/1999 | |
| WO | WO 00/44763 A2 | 8/2000 | |
| WO | WO 00/72799 A2 | 12/2000 | |
| WO | WO 00/73307 A2 | 12/2000 | |
| WO | WO 00/78774 A2 | 12/2000 | |
| WO | WO 01/40244 AI | 6/2001 | |
| WO | WO 01/40246 A1 | 6/2001 | |
| WO | WO 02/22630 A1 | 3/2002 | |
| WO | WO 02/102822 A1 | 12/2002 | |
| WO | WO 03/029264 A2 | 4/2003 | |
| WO | WO 03/086408 A1 | 10/2003 | |
| WO | WO 2005/107463 A1 | 11/2005 | |

OTHER PUBLICATIONS

Guo, British Journal of Pharmacology (2012) 166, 1846-1859.*
Barshes et al. Journal of Leukocyte Biology, vol. 77, May 2005.*
Berge, Journal of Pharmaceutical Sciences, vol. 66, No. 1, Jan. 1977.*
Gough, G.R. et al., "New Inhibitors of Platelet Aggregation. 5'-Phosphate, 5'-Phosphorothioate, and 5'-*O*-Sulfamoyl Derivatives of 2-Substituted Adenosine Analogues," *J. Med. Chem.* 21:520-525, American Chemical Society (1978).
Halbfinger, E. et al., "Molecular Recognition of Modified Adenine Nucleotides by the P2Y₁-Receptor. 1.A Synthetic, Biochemical. and NMR Approach," *J. Med. Chem.* 42:5325-5337, American Chemical Society (1999).

(Continued)

*Primary Examiner* — Layla Berry
(74) *Attorney, Agent, or Firm* — Sheridan Ross P.C.

(57) ABSTRACT

A phosphorylated $A_{2A}$ receptor agonist providing agonist properties on the $A_{2A}$ receptor after dephosphorylation the phosphorylated $A_{2A}$ receptor agonist comprises a ribosyl moiety and a purine moiety and being phosphorylated at the 5'-position of the ribose moiety except adenosine monophosphate (AMP), adenosine diphosphate (ADP) or adenosine triphosphate (ATP), a medicament containing the compound of the invention including ADP and the use of the compound of the invention including ATP and ADP for several medical indications e.g. inflammatory events. In particular, compounds of formula (I) are also disclosed.

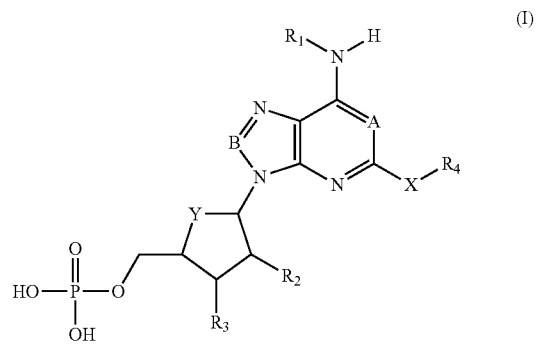

(I)

21 Claims, 7 Drawing Sheets

(56) References Cited

OTHER PUBLICATIONS

Hasan, A. et al., "2-Substituted Thioadenine Nucleoside and Nucleotide Analogues: Synthesis and Receptor Subtype Binding Affinities (1)," *Bioconjugate Chem.* 5:364-369, American Chemical Society (1994).

Kapetanovic, E. et al., "2-[(4-Bromo-2,3-dioxobutyl)thio]adenosine 5'-Monophosphate, a New Nucleotide Analogue That Acts as an Affinity Label of Pyruvate Kinase," *Biochem.* 24:7586-7593, American Chemical Society (1985).

Sullivan, G.W., "Adenosine $A_{2A}$ Receptor Agonists as Anti-Inflammatory Agents," *Curr. Opin. Invest. Drugs* 4:1313-1319, Thomson Scientific (2003).

International Search Report for International Application No. PCT/EP2007/052716, mailed on Aug. 8, 2007, European Patent Office, Rijswijk, Netherlands.

Kikugawa, K. et al., "Platelet Aggregation Inhibitors. 7. $^1$S-Substituted 2-Thiadenosine 5'-Monophosphates," *J. Med. Chem.* 16(12):1289-1391, American Chemical Society, United States (1973).

Francis, J.E. and Moskal, M.A., "A general synthesis of 5,7-diaminoimidazo[4,5- β]pyridine ribosides ("2-amino-1-deazaadenosines") from 5-amino-4-imidoazolecarboxamide riboside (AICA riboside)," *Can. J. Chem.* 70:1288-1391, National Research Council, Canada (1992).

Bulicz, J., et al.,"Synthesis and pharmacology of pyrido[2,3-*d*]pyrimidinediones bearing polar substituents as adenosine receptor antagonists," *Bioorg. Med. Chem.* 14(8):2837-2849, Elsevier Ltd., England (2006).

Ingall, A.H et al., "Antagonists of the platelet $P_{2T}$ receptor: a novel approach to antithrombotic therapy," *J. Med. Chem.* 42(2):213-220, American Chemical Society, United States (1999).

Kikugawa, K., et al., "Platelet aggregation inhibitors. IX. Chemical transformation of adenosine into 2-thioadenosine derivatives," *Chem. Pharm. Bull. (Tokyo)* 25(8):1959-1969, Pharmaceutical Society of Japan, Japan (1977).

Kikugawa, K., et al., "Platelet aggregation inhibitors. X. S-Substituted 2-thioadenosines and their derivatives," *Chem. Pharm. Bull. (Tokyo)* 25(10):2624-2627, Pharmaceutical Society of Japan, Japan(1977).

Knoblauch, B.H.A., et al.,"5-Substituted UTP derivatives as $P2Y_2$ receptor agonists," *European Journal of Medicinal Chemistry* 34(10):809-824, Editions scientifiques et médicales Elsevier SAS, France (1999).

Ludwig, J., "A new route to nucleoside 5'-triphosphates," *Acta. Biochim. Biophys. Acad. Sci Hung* 16(3-4):131-133, Akademiai Kiado, Hungary (1981).

Servos, J., et al.,"Catalytically active soluble ecto-5'-nucleotidase purified after heterologous expression as a tool for drug screening," *Drug Dev. Res.* 45(3-4):269-276, Wiley-Liss, Inc., United States (1998).

Yan, L. and Müller, C.E., "Preparation, properties, reactions, and adenosine receptor affinities of sulfophenylxanthine nitrophenyl esters: toward the development of sulfonic acid prodrugs with peroral bioavailability," *J. Med. Chem.* 47(4):1031-1043, American Chemical Society, United States (2004).

\* cited by examiner

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
agctgtctga catcgctcac cg                                    22

<210> SEQ ID NO 2
<211> LENGTH: 22
<212> TYPE: DNA
<213> ORGANISM: Artificial Sequence
<220> FEATURE:
<223> OTHER INFORMATION: Primer

```
<400> SEQUENCE: 2
cacatactgg cagcgcttca ag                                        22

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
ggaattctgc tcagtggggt ggatg                                     25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
cggatccggg ctcacgtcca tgcgc                                     25

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
agagaaacca tttattgttg acatctcc                                  28

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
agagaaacca tttattgttg acatctc                                   27

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
cactctgcct ctgtttgggt tca                                       23

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
gaattactga aggggagac tacac                                      25
```

```
<210> SEQ ID NO 9
<211> LENGTH: 16
<212> TYPE: DNA
<213> ORGANISM: Artificial Sequence
<220> FEATURE:
<223> OTHER INFORMATION: Primer

<400> SEQUENCE: 9
ccacagcctt ggcagc                                                   16

<210> SEQ ID NO 10
<211> LENGTH: 17
<212> TYPE: DNA
<213> ORGANISM: Artificial Sequence
<220> FEATURE:
<223> OTHER INFORMATION: Primer

<400> SEQUENCE: 10
cactcaagat tgtcagc                                                  17
```

PHOSPHORYLATED A2A RECEPTOR AGONISTS

The present invention pertains to a phosphorylated $A_{2A}$ receptor agonist, a medicament comprising a phosphorylated $A_{2A}$ receptor agonist, a use of a phosphorylated $A_{2A}$ receptor agonist as well as a method for identifying a phosphorylated $A_{2A}$ receptor agonist.

BACKGROUND OF THE INVENTION

Reference to Sequence Listing Submitted Electronically Via EFS-Web

The content of the electronically submitted sequence listing (Name: 2684_0030001_SEQLISTING_ascii.txt; Size: 2.227 bytes; and Date of Creation: Feb. 3, 2014) is herein incorporated by reference in its entirety.

$A_{2A}$ agonists are well known for their anti-inflammatory action. Respective agonists are disclosed e.g. in U.S. Pat. Nos. 5,877,180, 6,448,235, 6,514,949, 6,531,457, WO-A-00/44763. WO-A-00/78774, WO-A-01/40244, WO-A-01/40246, WO-A-02/22630, WO-A-02/102822, WO-A-03/029264, WO-A-93/08206, WO-A-93/23417, WO-A-93/23418, WO-A-95/30683, WO-A03/086408, WO-A-2005/107463, WO-A-99/34804, WO-A-00/72799, WO-A-00/73.307.

SUMMARY OF THE INVENTION

An object of the present invention was to provide a new class of compounds which can be administered systemically or locally and which are processed at the site of e.g. an inflammatory or other event being involved with the $A_{2A}$ receptor.

DETAILED DESCRIPTION OF THE INVENTION

Figure 1:
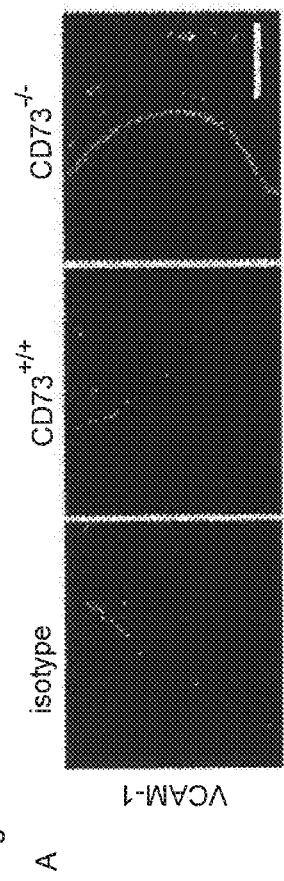
FIGS. 1A-C. Expression of the endothelial adhesion molecule VCAM-1 in carotid arteries. (A) Staining for VCAM-1 along the endothelial lining of carotid arteries; (B) mRNA transcripts for CD73; (C) Western blotting of whole carotid lysates.
Figure 1:
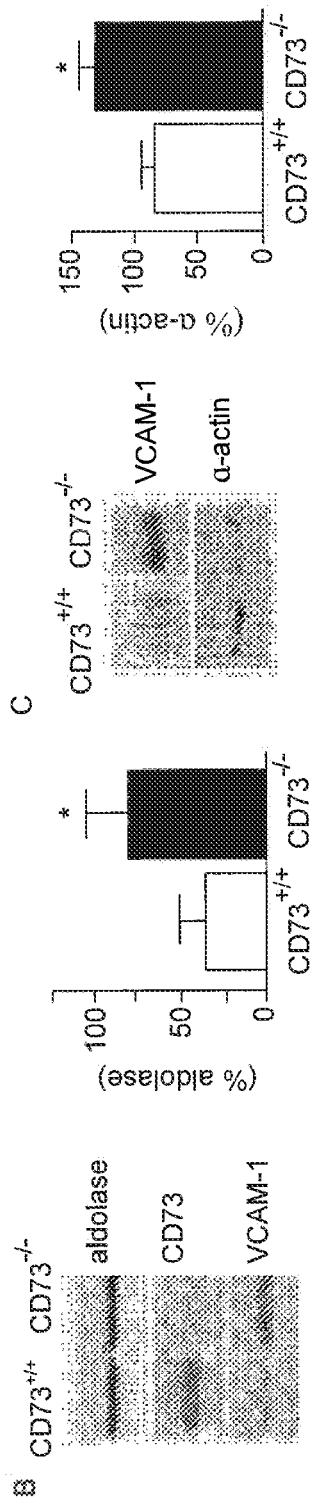
Figure 2:
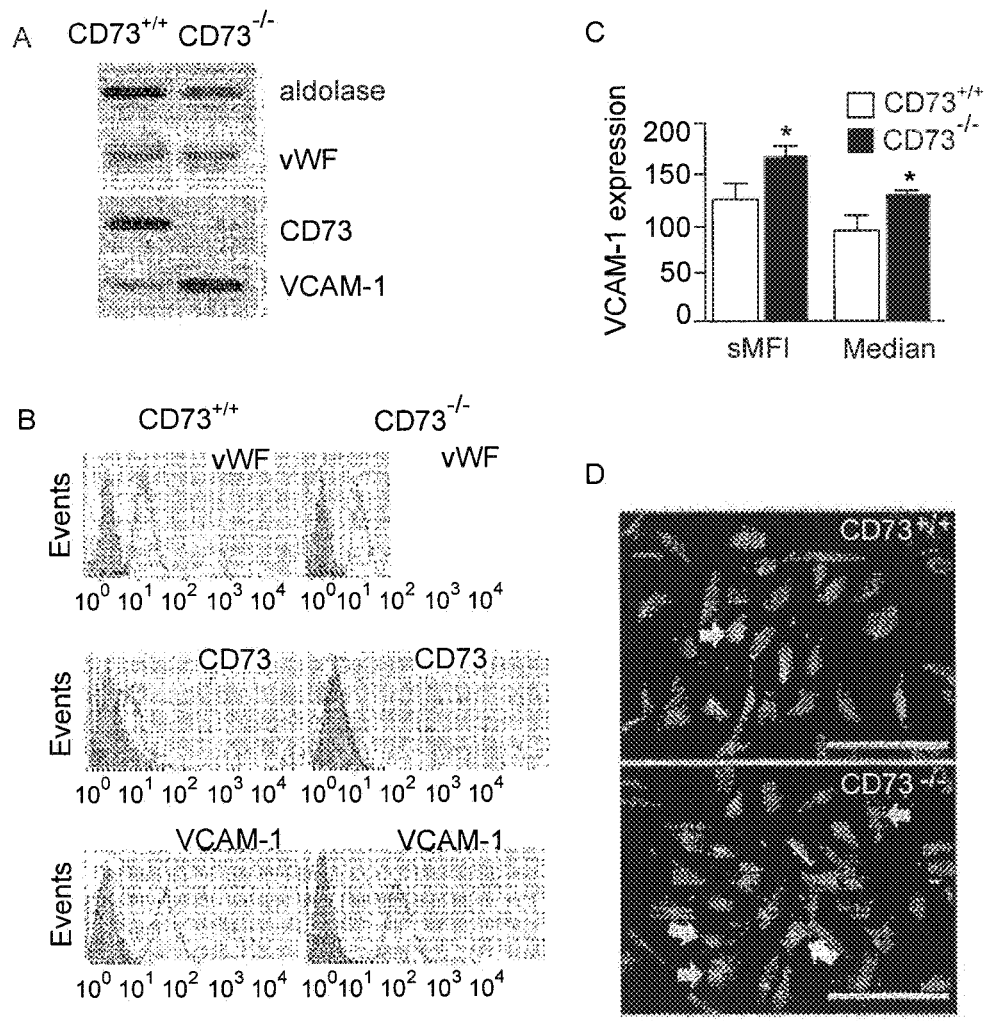
FIGS. 2A-D. Expression of VCAM-1 in cultured aortic ECs isolated from WT or $CD73^{-/-}$ mice. (A) mRNA transcripts for CD73; (B) Protein expression by flow cytometry; (C) Surface protein expression of VCAM-1; (D) Nuclear staining of cells for p65.
Figure 3:
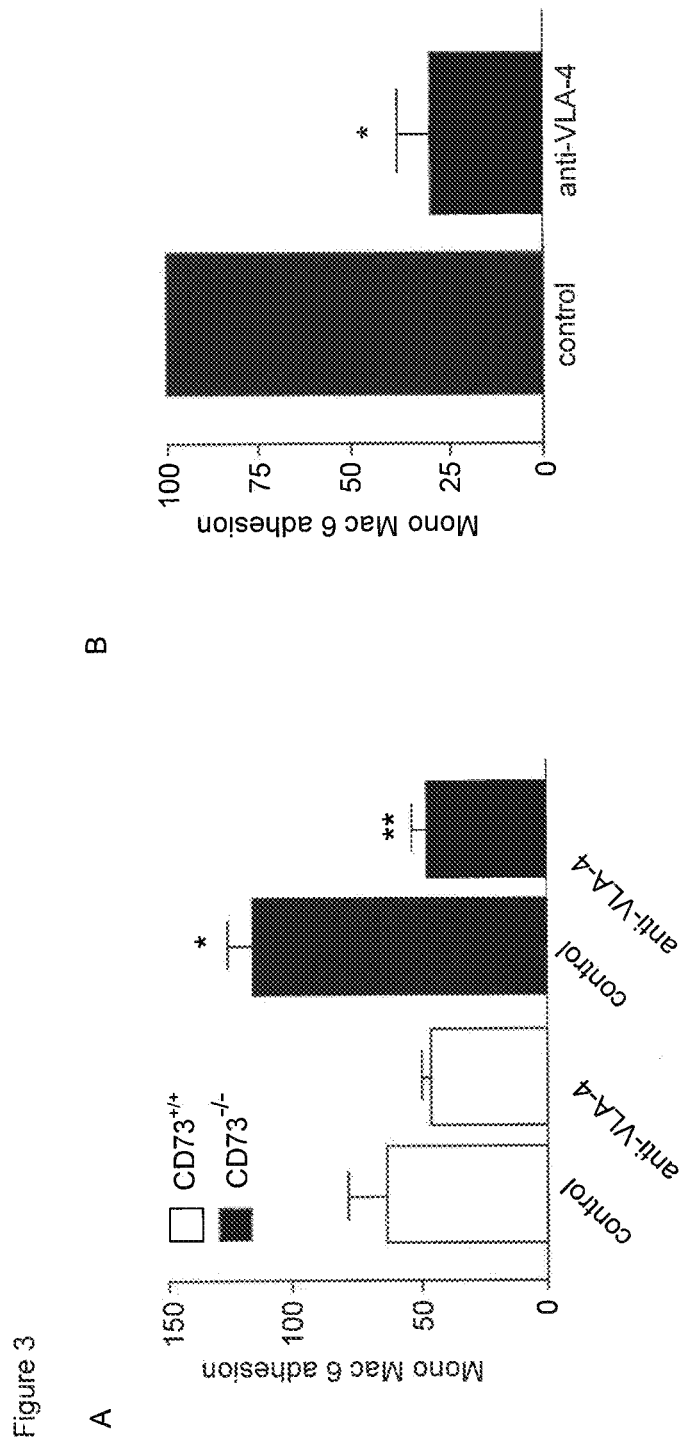
FIGS. 3A-B. In situ adhesion of monocytes under flow conditions and the contribution of VCAM-1 to monocyte accumulation in carotid arteries. (A) Arrest of monocytic cells; (B) Monocyte recruitment in carotid arteries.
Figure 4:
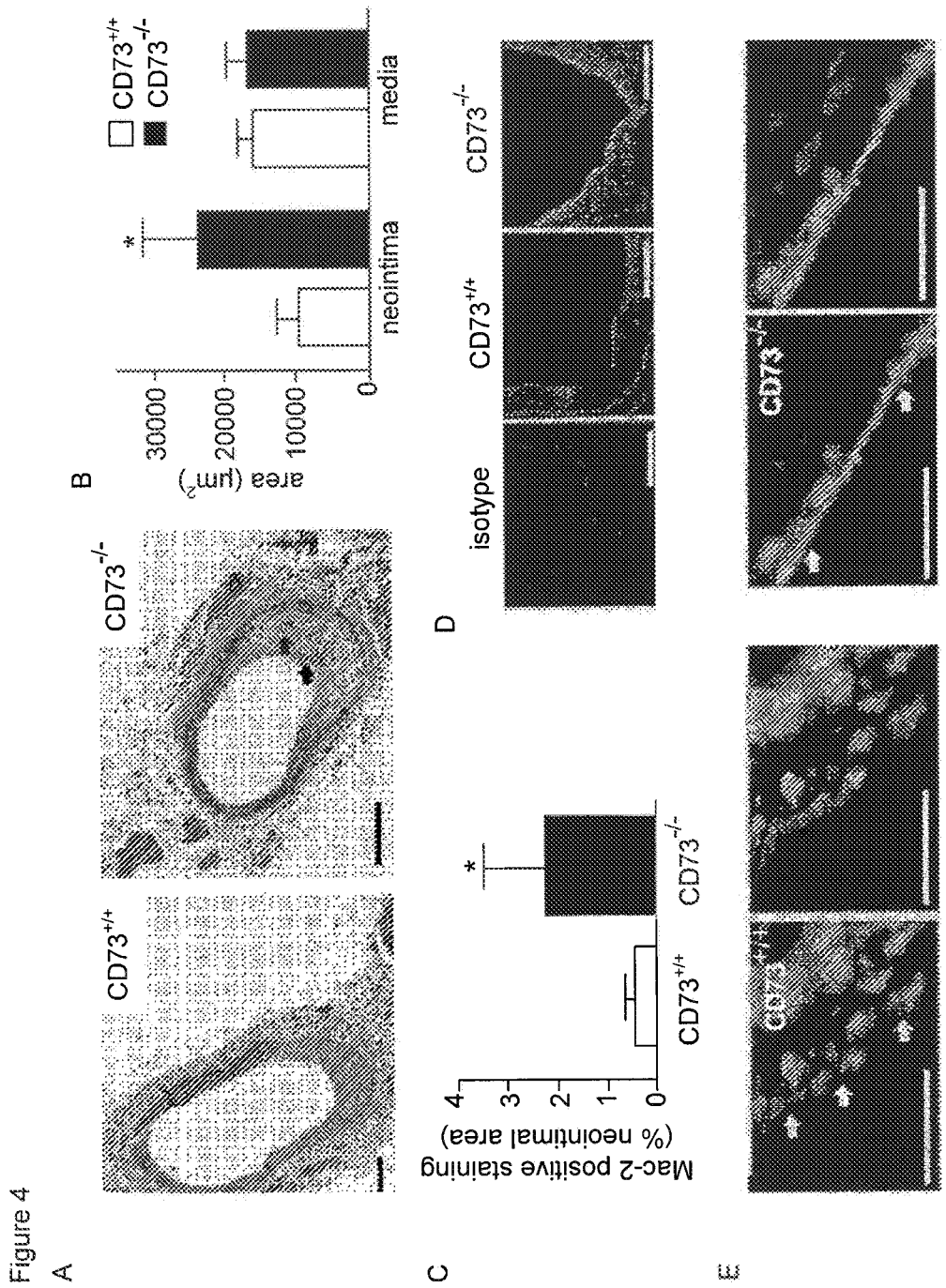
FIGS. 4A-D. The role of CD73 in neointimal plaque formation. (A) Plaque formation after injury; (B) Quantification of plaque formation after injury in (A); (C) Quantitative immunofluorescence macrophages in the neointima of mice; (D) Immunofluorescene staining of the expression of luminal VCAM-1 and P-selectin in carotid arteries; (E) Nuclear translocation of p50 as a marker of NF-κB activity in luminal cells.
Figure 5:
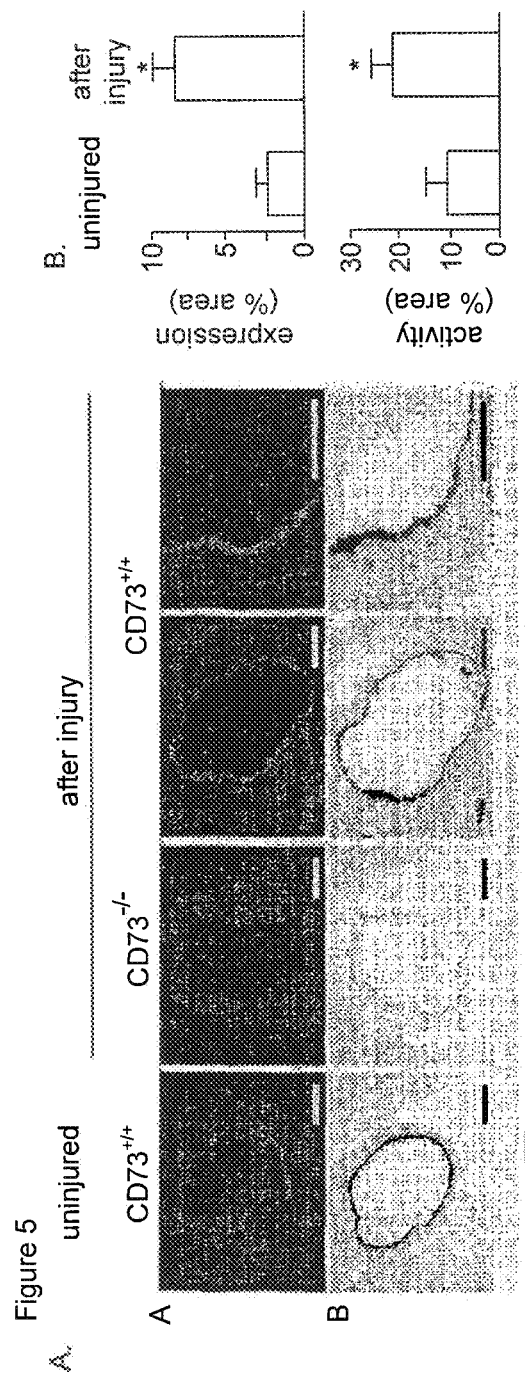
FIGS. 5A-B. Expression and enzymatic activity of CD73 after arterial injury at the shoulder and along the luminal lining covering the neointimal plaques.
Figure 6:
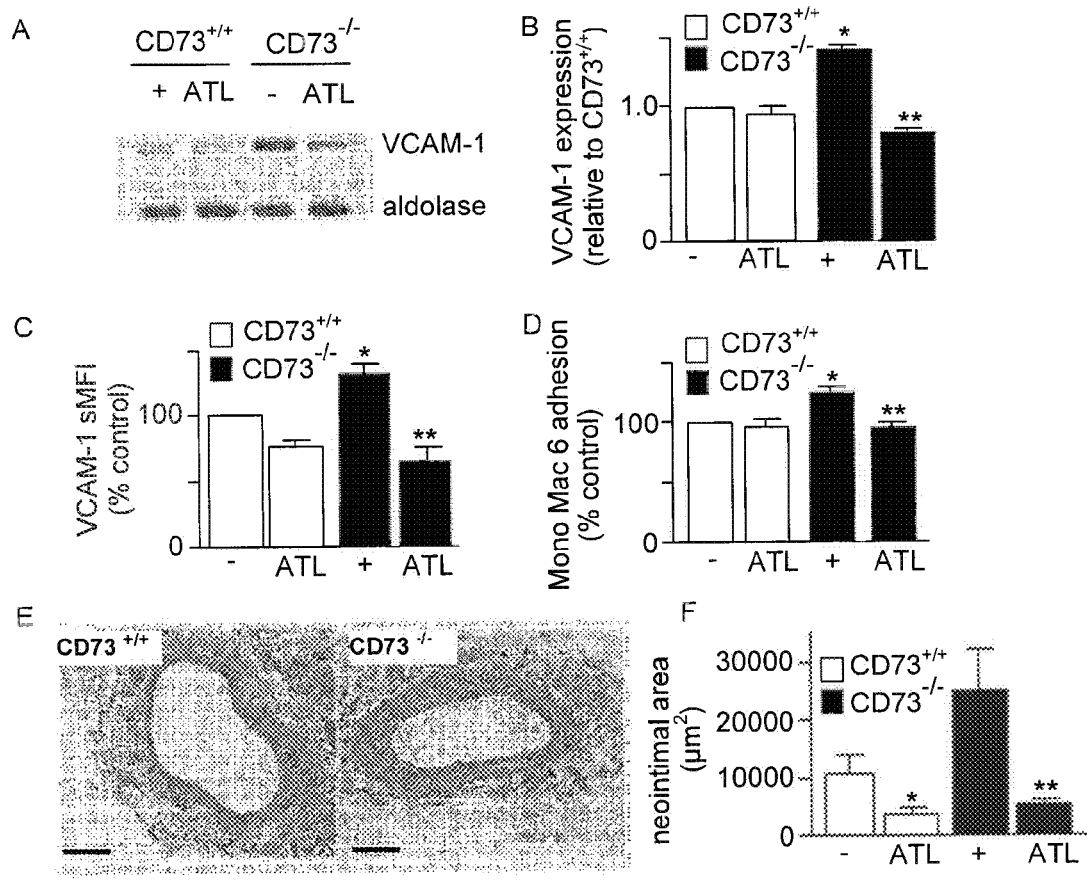
FIGS. 6A-F. Effects of a specific $A_{2A}$ adenosine receptor agonist. (A) In vitro VCAM-1 mRNA expression; (B) Quantification of expression in (A); (C) Determination of surface protein expression of VCAM-1 by flow cytometry; (D) Determination of monocyte arrest by flow cytometry; (E) Neointima formation in carotid arteries 4 weeks after injury; (F) Quantification of neointima formation in (E).

The present invention comprises compounds and methods of their use for the treatment of inflammatory activity in mammalian tissue. The inflammatory tissue activity can be due to pathological agents or can be due to physical, chemical or thermal trauma, or the trauma of medical procedures, such as organ, tissue or cell transplantation, angioplasty (PCTA), inflammation following ischemia/reperfusion, or grafting. The compound of the invention can be applied in a method for treating inflammation caused by diabetes particularly, diabetic kidney disease, e.g., diabetic nephropathy.

The compound of the invention is a phosphorylated $A_{2A}$ receptor agonist providing agonist properties on the $A_{2A}$ receptor after dephosphorylation the phosphorylated $A_{2A}$ receptor agonist comprises a ribosyl moiety and a purine moiety and being phosphorylated at the 5'-position of the ribose moiety except adenosine monophosphate (AMP), adenosine diphosphate (ADP) or adenosine triphosphate (ATP).

All $A_{2A}$ agonists so far reported serve as substrate of being phosphorylated to finally serve as a pro-drug. This only becomes activated by enzymatic activity in the body, predominantly by CD73.

The phosphorylated $A_{2A}$ receptor agonist of the invention is represented by a compound having the formula (I)

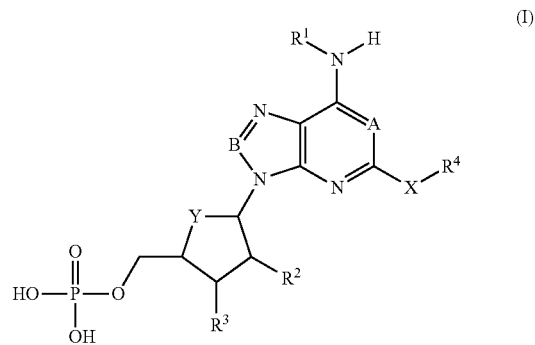

wherein:
A and B are independently of each other CH or N,
Y is selected from the group consisting of NH, O, S, C=O, and $CH_2$;
$R^1$ is hydrogen, ($C_1$-$C_5$) alkyl, alkenyl or alkoxy;
X is selected from the group consisting of O, S, NH, C=O, C=S, $O(CH_2)_{1-3}$, $N(CH_2)_{1-3}$, $NH(CH_2)_{1-3}$, $S(CH_2)_{1-3}$, NHN=N, NHN=$NCH_2$; C(O)—$(CH_2)_{1-3}$, C(S)—$(CH_2)_{1-3}$, C=N=N, C≡C, C≡C—$(CH_2)_{1-3}$;
$R^2$, $R^3$ are independently from each other $OR^5$, $NR^5R^6$, $SR^5$, wherein $R^5$ and $R^6$ are independently hydrogen, lower alkyl such as Me, Et, n-propyl, isopropyl, n-butyl, sec-butyl, tert-butyl; alkoxy, alkylamino, $C_1$-$C_3$ alkylthio;
$R^4$ is selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy,
an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR' wherein R and R' are independently of each other selected from the group consisting of ($C_1$-$C_4$) alkyl or ($C_1$-$C_4$) alkenyl residues. and physiologically acceptable salts such as sodium, potassium, ammonium, triethylammonium, trimethylammonium, or other substituted ammonium salts.

In particular, the phosphorylated $A_{2A}$ receptor agonist of the invention is represented by a compound having the formula (I) wherein A and B are CH;

Y is O;

$R^1$ is selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl wherein 1 to 4 ring atoms are independently selected from nitrogen, oxygen or sulfur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, wherein R and R' are independently of each other selected from the group consisting of ($C_1$-$C_4$) alkyl or ($C_1$-$C_4$) alkenyl residues;

X is selected from the group consisting of O, S, NH, C=O, C=S, O(CH$_2$)$_{1-3}$N(CH$_2$)$_{1-3}$, NH(CH$_2$)$_{1-3}$, S(CH$_2$)$_{1-3}$, NHN=N, NHN=NCH$_2$; C(O)—(CH$_2$)$_{1-3}$, C(S)—(CH$_2$)$_{1-3}$, C=N=N, C≡C, C≡C—(CH$_2$)$_{1-3}$, $R^2$, $R^3$ are independently from each other OR$^5$, NR$^5$R$^6$, SR$^5$, wherein R$^5$ and R$^6$ are independently hydrogen, lower alkyl such as Me, Et, n-propyl, isopropyl, n-butyl, sec-butyl, tert-butyl;

$R^4$ is selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl wherein 1 to 4 ring atoms are independently selected from nitrogen, oxygen or sulfur, an unsubstituted or substituted 5- to 10-membered heteroalicyclic ring wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR' wherein R and R' are independently of each other selected from the group consisting of ($C_1$-$C_4$) alkyl or ($C_1$-$C_4$) alkenyl residues. and physiologically acceptable salts such as sodium, potassium, ammonium, triethylammonium, trimethylammonium, or other substituted ammonium salts.

In another embodiment of the invention, the phosphorylated $A_{2A}$ receptor agonist of the invention comprises a compound wherein X is S.

Individual phosphorylated $A_{2A}$ receptor agonist of the invention are selected from the group consisting of 2-(Cyclohexylthio)adenosine-5'-monophosphate;
2-(Cyclohexylmethylthio)adenosine-5'-monophosphate;
2-(Cyclohexylethylthio)adenosine-5'-monophosphate;
2-(Propylthio)adenosine-5'-monophosphate;
2-(Allylthio)adenosine-5'-monophosphate;
2-(Hexylthio)adenosine-5'-monophosphate;
2-(Cyclopentylmethylthio)adenosine-5'-monophosphate;
2-(Benzylthio)adenosine-5'-monophosphate; and
2-(Phenylethylthio)adenosine-5'-monophosphate, of course also in form of salts.

A medicament of the invention comprises a phosphorylated $A_{2A}$ receptor agonist providing agonist properties on the $A_{2A}$ receptor after dephosphorylation except adenosine triphosphate (ATP).

In particular, the medicament comprises the aforementioned compounds of formula (I) also in the more specified individual compounds.

The medicament is suitable for the treatment of acute and chronic inflammation. It comprises treating inflammation caused by immune response of transplanted tissue (bone marrow, skin, pancreatic islands, lung, kidney, heart, liver, cornea). Chronic inflammation includes arteriosclerosis, arthritis and Crohn's disease. Treatment also includes traumatic spinal cord injury and restenosis of arteries after percutaneous transluminal angioplasty (PTA).

The phosphorylated $A_{2A}$ receptors of the invention as well as AMP, ADP, ATP or combinations thereof can be used for the manufacturing of a medicament for the treatment of diseases related with or caused by acute or chronic inflammatory, hypotensive, psychotic, or asthmatic events.

The present invention provides a therapeutic method for treating biological diseases that includes the administration of an effective amount of a suitable antibiotic agent, antifungal agent or antiviral agent in conjunction with an $A_{2A}$ adenosine receptor agonist. If no anti-pathogenic agent is known the $A_{2A}$ agonist can be used alone to reduce inflammation, as may occur during infection with antibiotic resistant bacteria, or certain viruses such as those that cause SARS or Ebola. Optionally, the method includes administration of a type IV PDE inhibitor. The $A_{2A}$ adenosine receptor agonist can provide adjunctive therapy for treatment conditions such as, the inflammation, caused by sepsis, for example, human uremic syndrome when administered with antibiotics in the treatment of bio-terrorism weapons, such as anthrax, tularemia, *Escherichia coli*, plague and the like. The present invention also provides adjunctive therapy for treatment of lethal bacterial, fungal and viral infections such as anthrax, tularemia, *escherichia* and plague comprising administration of an antibacterial agent, an antifungal agent or an antiviral agent in conjunction with selective, $A_{2A}$ adenosine receptor agonists.

The present invention provides a therapeutic method for treating biological diseases that provoke inflammation either alone or in combination with a disease killing medicine. These include bacteria in combination with antibiotics, including but not limited to bacteria that cause anthrax, tularemia, plague, lyme disease and anthrax. Also included are viruses including but not limited to those that cause RSV, severe acute respiratory syndrome (SARS).

Subject matter of the present invention is also a method for identifying a phosphorylated $A_{2A}$ receptor agonist comprising the steps of:
providing an $A_{2A}$ receptor containing entity,
adding an established $A_{2A}$ receptor agonist to said entity and
determining the degree of competition of a putative $A_{2A}$ receptor agonist with the established $A_{2A}$ receptor agonist or determining the degree of binding of a putative $A_{2A}$ receptor agonist to said entity determining in a functional assay whether an identified $A_{2A}$ receptor agonist is able to elicit the physiological response of an $A_{2A}$ receptor agonist.

In one embodiment of the method for identifying a phosphorylated $A_{2A}$ receptor agonist the degree of binding of the putative $A_{2A}$ receptor agonist to said entity is the $K_D$ of the putative $A_{2A}$ receptor agonist to the $A_{2A}$ receptor.

In a further embodiment of the method for identifying a phosphorylated $A_{2A}$ receptor agonist the degree of competition of the putative $A_{2A}$ receptor agonist with the established $A_{2A}$ receptor agonist is the $EC_{50}$ value.

Typically, the putative $A_{2A}$ receptor agonist of the invention is also a substrate of ecto-5'-ectonucleotidase (CD73).

In yet another embodiment of the method for identifying a phosphorylated $A_{2A}$ receptor agonist the physiological response of an identified $A_{2A}$ receptor agonist is validated by an animal model. In order to validate treatment, mice will be anesthetized and osmotic mini-pumps (model 1003D; ALZA) will be implanted. The pumps release either vehicle (0.01% DMSP in PBS) or medicament (about 10 ng/kg/min).

The phosphorylated A2s receptor agonists of the invention may be regarded as pro-drugs which are hydrolyzed specifically by ecto-5'-ectonucleotidase (CD73) to the dephosphorylated nucleoside derivative which acts as receptor agonist. Also dephosphorylation by phosphatases which non-specifically dephosphorylate the phosphorylated $A_{2A}$ receptor agonists of the invention may occur. In these cases the phosphorylated $A_{2A}$ receptor agonists of the invention do not require high substrate affinity to ecto-5'-ectonucleotidase (CD73). From Table 1 some data can be derived concerning substrate specificity of the phosphorylated $A_{2A}$ receptor agonists of the invention.

The use of the phosphorylated $A_{2A}$ agonists of the invention as pro-drugs has the following advantages:
  CD73 is localized on the outer surface of endothelial cells of large and small arteries as well as on inflammatory cells such as macrophages and T-lymphocytes.
  CD73 is upregulated on the endothelium of inflamed tissue. Examples are
    Proliferation of neointima after wire-induced injury in the carotid artery (mouse)
    Plasma levels of CD73 is upregulated after retro-orbital blood withdrawal (mouse)
    Upregulated in a well-established mouse model of arteriosclerosis (ApoE-mouse)
  On the endothelium the predominant enzyme for AMP degradation is CD73. Alkaline phosphatase which also breaks down AMP is usually not present. Furthermore Alkaline phosphatase is a high $K_m$ enzyme as compared to the low $K_m$ of CD73.
  Using phosphorylated $A_{2A}$ agonists as a pro-drug, the site of formation of the dephosphorylated derivative is identical with the site of action in the inflamed tissue.
  Since site of formation and site of action are identical, lower concentrations of the pro-drug are expected to be required as compared to a pure $A_{2A}$ agonist. This should go in parallel with reduced systemic side effects.

The compounds of the invention are phosphorylated in the ribosyl moiety of the agonist with the proviso that the 5'-position is phosphorylated with a monophosphate, diphosphate or triphosphate moiety. For structural details of the purine moiety, generic formula as well as methods of synthesis, it is referred to the numerous references which are well known to the skilled person.

The concept of the invention is based on the finding (although not being bound by any theory) that ecto-5-nucleotidases such as CD73 are up-regulated at the site of an inflammatory event. This is shown by FIG. 1 to 7.

One result of the studies underlying the invention show that CD73 is markedly upregulated in atherosclerotic plaques. Highly inflamed vulnerable atherosclerotic lesions are characterized by high local concentration of CD73.

This makes CD73 an excellent target for detecting vulnerable lesions as a new measure of detecting clinical cardiovascular risk with non-invasive imaging methods. This includes e.g. use of antibodies or peptides directed at CD73 which are linked to an appropriate label such as a radiotracer or NMR visible support. (Jaffer F. A. and Weissleder R. "Seeing within: molecular imaging of the cardiovascular system," Circulation research 2004, 94:433-455 (review)).

Also subject matter of the present invention is a therapeutic method for treating inflammation caused by an immune response to transplanted tissue, comprising the administration to a patient in need thereof of an effective amount of an $A_{2A}$ adenosine receptor agonist. In particular, the immune response is a transplant rejection, or graft versus host disease. The transplantation may comprise an organ, tissue or cell transplantation. In particular, the cells are bone marrow, skin, or pancreatic islets. In a further embodiment the organ is a cornea, kidney, lung, liver, or heart.

To elucidate the underlying molecular mechanism of a substantial accumulation of monocytes on endothelium, the expression of the endothelial adhesion molecule VCAM-1 was investigated in carotid arteries by immunofluorescence. While VCAM-1 expression was hardly detectable in carotid arteries of WT mice, consistent with a marginal constitutive expression, staining for VCAM-1 was strongly increased along the endothelial lining of carotid arteries in CD73$^{-/-}$ mice (FIG. 1A). In contrast, luminal ICAM-1 expression was constitutively detectable in WT carotid arteries, but rather decreased in arteries of CD73$^{-/-}$ mice (not shown). Expression of these adhesion molecules was further analyzed by RT-PCR in arteries collected from WT or CD73$^{-/-}$ mice. While mRNA transcripts for CD73 could only be detected in arteries of WT but not in CD73$^{-/-}$ mice (FIG. 1B), confirming the genetic deletion of CD73 (FIG. 1B), expression of VCAM-1 mRNA in line with the immunofluoresence results was low in WT arteries but markedly increased in CD73−/− arteries (FIG. 1B). In contrast, the expression of ICAM-1 mRNA was unaltered (not shown). These remarkable differences were further substantiated by Western blotting of whole carotid lysates, demonstrating a marked up-regulation of VCAM-1 protein in CD73$^{-/-}$ compared to WT carotid arteries (FIG. 1C).

Since staining of VCAM-1 was mostly confined to the luminal lining, we further analyzed its expression in cultured aortic ECs isolated from WT or CD73$^{-/-}$ mice. While a strong mRNA expression of vWF was observed in ECs isolated from WT and CD73$^{-/-}$ mice, confirming their endothelial phenotype, CD73 mRNA could only be detected in ECs of WT but not CD73$^{-/-}$ mice (FIG. 2A). Consistent with results obtained from carotid arteries, VCAM-1 mRNA expression was markedly up-regulated in CD73$^{-/-}$ versus WT ECs. Protein expression was further analyzed by flow cytometry. While both WT and CD73$^{-/-}$ ECs displayed positive staining for vWF, an absence of CD73 was confirmed in CD73$^{-/-}$ ECs (FIG. 2B). Compared to WT ECs, the surface protein expression of VCAM-1 was increased in CD73$^{-/-}$ ECs (FIG. 2B,C). Together, these results imply that the constitutive balance in the expression profile of arterial ECs is shifted towards a more pro-inflammatory phenotype in the absence of CD73.

Given that adenosine can block the activation of NF-κB in different cells, as wells as the pivotal role of NF-κB in the transcriptional regulation of pro-inflammatory and anti-apoptotic genes, including VCAM-1, we analyzed whether CD73 deficiency modulates the nuclear translocation of p65 as a marker for NF-κB activity by immunofluorescence in vitro. As compared to WT ECs, the proportion of cells with nuclear staining for p65 was significantly increased in $CD73^{-/-}$ ECs (19.4±2.0% vs. 49.1±3.6%, P<0.0001, see arrows in FIG. 2D).

Since VLA-4 binding to VCAM-1 is known to mediate mononuclear cell adhesion, next explored was the propensity of $CD73^{-/-}$ versus WT ECs to support the adhesion of monocytes under flow conditions and the contribution of VCAM-1 to monocyte accumulation in $CD73^{-/-}$ carotid arteries in situ. Compared with WT ECs, the arrest of monocytic cells was significantly increased in $CD73^{-/-}$ ECs (FIG. 3A) and inhibited by antibody blockade of the VCAM-1 receptor VLA-4 (FIG. 3A). ICAM-1 was not involved (not shown). Similarly, increased monocyte recruitment in carotid arteries of $CD73^{-/-}$ mice perfused ex vivo was significantly inhibited by blockade of VLA-4 (FIG. 3B). Background arrest of monocytes in WT arteries was negligible and unaffected by blocking VLA-4 (not shown). These data demonstrate the crucial involvement of VLA-4/VCAM-1 interactions in mediating increased monocyte arrest in arteries of $CD73^{-/-}$ mice.

Since inflammatory leukocyte recruitment is instrumental in neointimal hyperplasia, lesions in carotid arteries were analyzed 4 weeks after wire-induced injury to investigate the role of CD73 in neointimal plaque formation. Compared with WT mice, the genetic deletion of CD73 significantly enhanced plaque formation after injury, as evidenced by an increase in neointimal area, while the medial area was unaffected (FIG. 4A, B). Quantitative immunofluorescence further revealed a significant increase in the relative content of macrophages in the neointima of $CD73^{-/-}$ mice (FIG. 4C). Interestingly, $CD73^{-/-}$ but not WT carotid arteries frequently contained erythrocytes within the neointimal lesion (0.9±0.3% vs. 0.1±0.1% area, P<0.05, FIG. 4A, see arrows) indicative of intraplaque hemorrhage.

As shown by immunofluorescene staining, the increase in the expression of luminal VCAM-1 and P-selectin in $CD73^{-/-}$ versus WT carotid arteries was even more pronounced after wire-injury when compared to the up-regulation in uninjured $CD73^{-/-}$ arteries (FIG. 4D, not shown) and was associated with an increase in nuclear translocation of p50 as a marker of NF-κB activity in luminal cells (FIG. 4E). These data reveal that the pro-inflammatory EC phenotype of $CD73^{-/-}$ mice promotes neointimal hyperplasia and monocyte recruitment. Notably, both expression and enzymatic activity of CD73 were up-regulated after arterial injury at the shoulder and along the luminal lining covering the neointimal plaques (FIG. 5A,B). This implies that a compensatory up-regulation of CD73 may occur after injury.

To investigate whether the loss of extracellular adenosine is responsible for the shift towards a more pro-inflammatory state in $CD73^{-/-}$ mice, the effects of a specific $A_{2A}$ adenosine receptor agonist (ATL-146e) were explored. In vitro, treatment with ATL-146e reduced the elevated VCAM-1 mRNA expression in $CD73^{-/-}$ ECs to levels seen in WT ECs as analyzed by PCR (FIG. 6A,B). Flow cytometry further demonstrated that ATL-146e reversed the increased surface protein expression of VCAM-1 in $CD73^{-/-}$ ECs and slightly diminished its expression in WT ECs (FIG. 6C). Concomitantly, the reduction in VCAM-1 expression by ATL-146e was paralleled by an inhibition of the monocyte arrest to $CD73^{-/-}$ ECs, while monocyte arrest to WT ECs was not affected by the treatment with ATL-146e (FIG. 6D).

In order to functionally analyze underlying mechanisms of CD73 deficiency in vivo, WT and $CD73^{-/-}$ mice were treated by continuous infusion with ATL-146e for 4 weeks. Confirming previous findings, administration of ATL-146e significantly inhibited neointima formation in WT carotid arteries 4 weeks after injury in comparison to control WT mice (FIG. 6E, F). Importantly, ATL-146e completely prevented neointimal hyperplasia in $CD73^{-/-}$ carotid arteries, as compared to control $CD73^{-/-}$ mice (FIG. 6E, F) and reduced the neointimal area to levels observed in WT mice. These data show that the more pro-inflammatory phenotype due to the absence of CD73 can be completely reversed by activation of the adenosine $A_{2A}$ receptor and imply that under physiological conditions CD73 generating extracellular adenosine may participate in the resolution of excessive inflammation.

The following methods were employed:

Mouse Model of Carotid Artery Injury

Male, 6-12 week old $CD73^{-/-}$ or WT NMRI mice (n=6-8) were left untreated or fed an atherogenic diet containing 21% fat for one week before and up to 4 weeks after injury. Transluminal carotid artery injury was induced by 4 rotational passes of a 0.36-mm guide-wire. After 6 days of diet and one day before carotid injury, some mice (n=10 per group) were anesthetized and underwent implantation of a primed, 28-day osmotic pump (model 2004, Alza Corp) placed subcutaneously via transverse midscapular incision for continuous treatment with ATL (0.004 µg/kg per minute; 200 µL of 1% dimethyl sulfoxide in saline; kind gift from G. W. Sullivan and J. Linden, University of Virginia). Arteries were harvested by in situ perfusion fixation with 4% paraformaldehyde and embedded in paraffin. Animal experiments were approved by local authorities and complied with the German animal protection law.

Morphometry, Immunhisto- and Enzyme Histochemistry

Neointimal and medial areas were quantified in serial 5 µm sections of common carotid arteries within a standardized distance from the bifurcation (50-250 µm) stained with Movat pentachrome Areas within the external elastic lamina (EEL), internal elastic lamina (TEL) and lumen (L) were determined by computer-assisted planimetry (Diskus software, Hilgers). Neointimal area was defined as IEL-L, medial area as EEL-TEL. The relative content of macrophages in the neointima was determined in serial sections of the LCA within 300 µm from the bifurcation (6 per mouse, each 50 µm apart). Immunohistochemistry staining was performed using isotype controls (Santa Cruz) or Abs to Mac-2 (CL8942AP, Cedarlane), CD73 (BD Biosciences), p50 (NLS, Santa Cruz) reacted with FiTC-conjugated mAb (Boehringer Mannheim) and VCAM-1 (C-19, Santa Cruz) and ICAM-1 (M-19, Santa Cruz) detected by a biotin-conjugated secondary Ab visualized by Vectastain ABC-AP and Vector Red Substrate kit (Vector Labs). Ecto-5'-nucleotidase activity was localized as described. Images were recorded using a Leica DMLB microscope and CCD camera. CD73 activity and expression was quantified in uninjured carotid arteries and 4 weeks after injury (n=3 each, 3 section per mouse) using AnalySIS software (Soft-Imaging Systems).

Endothelial Cell Isolation and Cell Culture

Mouse aortal ECs were cultured as described. Six mL of type I rat tail collagen (4 mg/mL) combined with 0.1 M NaOH, 3.5 mL 3×DMEM and 5.25 mL of 1×DMEM supplemented with 30% FCS was aliquoted into a 24 well plate, allowed to gel at 37° C. for 1 hour and equilibrated overnight in complete EC medium: RPMI-1640 supplemented with 20% heat inactivated FCS, 2-mercaptoethanol (4 L/L), gentamicin (10 g/mL) and EC growth supplement (50 g/mL, BD Biosciences). Aortas from $CD73^{-/-}$ or WT mice cut into circular rings were opened longitudinally and placed luminal side down onto the collagen gel. After 2 days, complete medium was added and changed every third day. After 10 days, aortic segments were removed and the collagen gel digested with 0.3% collagenase H. Then, ECs were grown in complete medium and used between passages 2-8. Some ECs were treated with ATL-146e (10 µM) for 6 hours. Mono Mac 6 cells were maintained as described.

Immunofluorescence and Flow Cytometry

For immunofluorescence, confluent ECs on glass chamber slides were fixed in methanol, permeabilized with 0.5% triton and reacted with p65 (C-20, Santa Cruz) or isotype control and FITC-conjugated secondary Ab (Boehringer Mannheim). For flow cytometry, ECs were reacted with saturating concentrations of CD73 and VCAM-1 mAbs (BD Pharmingen) or isotype controls. Some ECs were permeabilized in 0.1% Triton-X for 5 min at RT and stained with vWF Ab (clone F-3520, Sigma) or isotype control. After incubation for 30 min at RT, primary Ab binding was detected using a FITCconjugated secondary Ab (Boehringer Mannheim) and analyzed in a FACSCalibur (BD Biosciences). Specific mean fluorescence intensity was determined by subtracting isotype control staining.

Ex vivo Perfusion of Carotid Arteries after Wire-Injury

Carotid arteries from $CD73^{-/-}$ or WT mice were isolated for ex vivo perfusion as described, transferred onto a microscope stage (saline immersion objective) and perfused with Mono Mac 6 cells ($10^6$/mL) labeled with calcein-AM (Molecular Probes) in MOPS-buffered physiological salt solution at 4 µL/min. Cells were left untreated or pretreated with anti-VLA-4 mAb (10 µg/mL; clone HP2/1, Immunotech). Adhesive interactions with the vessel wall were recorded using stroboscopic epifluorescence illumination (Drelloscop 250, Drello, Monchengladbach, Germany) and firmly adherent cells were counted after 10 min of perfusion and expressed as percentage of untreated control (n=3).

RT-PCR and Real-Time Quantitative RT-PCR

RNA was prepared using the RNAqzeous-Micro isolation kit (Ambion) and RNeasy Mini kit (Qiagen) and reverse-transcribed into cDNA using Mo-MLV RT (Invitrogen). PCR was performed with 20 ng eDNA using Taq DNA polymerase (Promega) and specific primer pairs (RT-PCR: aldolase, 5'-AGCTGTCTGACATCG CTCACCG-3' (SEQ ID NO: 1), 5'-CACATACTGGCAGCGCTTCAAG-3' (SEQ ID NO: 2); $CD73^9$; vWF, 5'-GGAATTCTGCTCA-GTGGGGTGGATG-3 (SEQ ID NO: 3), 5'-CGGATC-CGGGCTCACGTCCATGCGC-3 (SEQ ID NO: 4); VCAM-1, 5'-AGAGAAACCATTTATTCTT-GACATCTCC-3' (SEQ ID NO: 5), 5'-AGAGAAACCATT-TATTGTTGACATCTC-3' (SEQ ID NO: 6), and products were separated by agarose gel electrophoresis. Densitometry of gel images was performed using Scion Image software. Real time RT-PCR was performed using the QuantiTect SYBR Green PCR kit and specific primer pairs (VCAM-1, 5'-CACTCTGCCTCTGTTTGGGTTCA-3 (SEQ ID NO: 7), 5'-GAATTACTGAAGGGGGAGACTACAC-3 (SEQ ID NO: 8); GAPDH, 5'-CCACAGCCTTGGCAGC-3 (SEQ ID NO: 9), 5'-CACTCAAGATTGTCAGC-3 (SEQ ID NO: 10)).

Adhesion Assay

Laminar flow assays were performed as described. ECs were perfused with Mono Mac 6 cells ($0.5 \times 10^6$/mL) pre-treated with or without anti-VLA-4 (10 g/mL, Immunotech) at 1.5 dyn/cm². The numbers of firmly arrested and rolling cells were quantified after 4 min in multiple (>10) fields by analyzing images recorded by video microscopy, and expressed as cells/mm²

Western Blotting

After perfusion with PBS, whole carotid arteries of WT and $CD73^{-/-}$ mice (n=4 each) were excised and boiled in Laemmli buffer. Western blotting for β-actin (clone AC-74, Sigma) and VCAM-1 (sc-1504, Santa Cruz) was performed using the enhanced chemiluminescence system (Amersham-Biosciences) and analyzed by densitometry (Scion Image software).

Statistical Analysis

Data represent mean±SEM and were compared by either 2-tailed Student's t test or 1-way ANOVA followed by Newman-Keuls post-test where appropriate (InStat software, GraphPad). Differences with P<0.05 were considered to be statistically significant.

Figure 7:
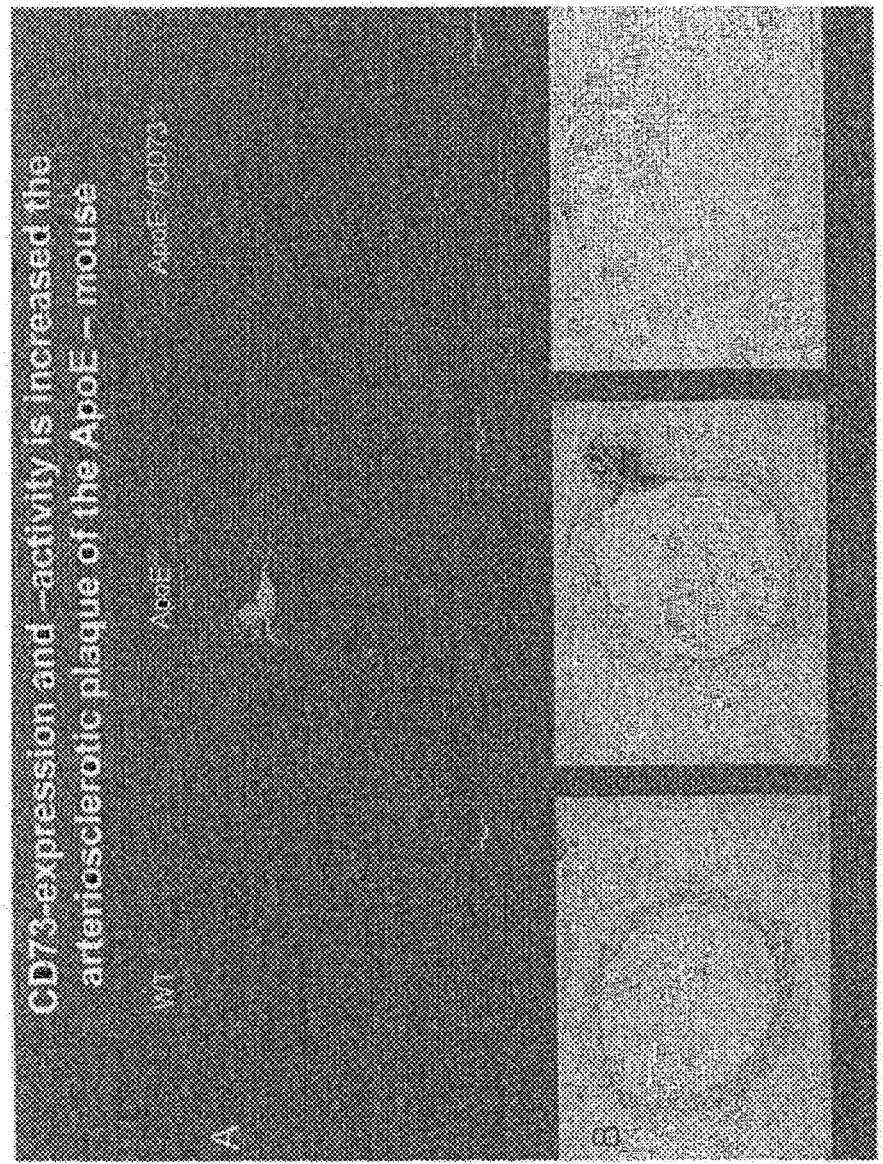
FIG. 7. CD73-expression and activity in the arteriosclerotic plaque of the ApoE-mouse.

The FIG. 7 shows the increased CD73-expression and -activity in the arteriosclerotic plaque of the ApoE-mouse. FIG. 7 shows a massive up-regulation of CD73 directly in the arteriosclerotic plaque of the ApoE-mouse. These mice are standard experimental model in arteriosclerosis research. The results stem from 6 month old mice which were fed with a normal diet. FIG. 7a shows immuno chemistry of CD73, FIG. 7b shows enzymatic activity with a led phosphate precipitation method. The double knockout CD73/ApoE demonstrates the specificity of the reaction.

General Synthetic Procedures

All commercially available reagents were obtained from various producers (Acros, Aldrich, Fluka, Merck, and Sigma) and used without further purification. Solvents were used without additional purification or drying, unless otherwise noted. The reactions were monitored by thin layer chromatography (TLC) using aluminum sheets with silica gel 60 $F_{254}$ (Merck). Column chromatography was carried out with silica gel 0.060-0.200 mm, pore diameter ca. 6 nm. Mass spectra were recorded on an API 2000 (Applied Biosystems, Darmstadt, Germany) mass spectrometer (turbo ion spray ion source) coupled with a Waters HPLC system (Agilent 1100) using a Phenomenex Luna 3µ C18 column. $^1$H-, $^{31}$P-, and $^{13}$C-NMR spectra were performed on a Bruker Avance 500 MHz spectrometer. DMSO-$d_6$, MeOD-$d_4$, or $D_2O$ were used as solvents as indicated below. $^{31}$P-NMR spectra were recorded at room temperature; orthophosphoric acid (85%) was used as an external standard. Shifts are given in ppm relative to the external standard ($^{31}$P-NMR) or relative to the remaining protons of the deuterated solvents used as internal standard ($^1$H, $^{13}$C). Elemental microanalyses were performed on a VarioEL apparatus at the Pharmaceutical Institute, Bonn-Endenich, University of Bonn. Melting points were determined on a Buchi 530 melting point apparatus and are uncorrected. Purity of the prepared nucleosides was checked by TLC on silica gel 60 $F_{254}$ (Merck) aluminum plates, using dichloromethane:methanol (9:1) as the mobile phase.

Purity of the prepared nucleotides was confirmed by HPLC on an RP-HPLC column (Knauer 20 mm ID, Eurospher-100 C18). The column was eluted with a solvent gradient of 0-10% of acetonitrile in 50 mM aq. $NH_4HCO_3$ buffer for 40 min at a flow rate of 5 ml/min. UV absorption was detected at 254 nm. The purity of the nucleotide samples was checked in a second chromatography system by dissolving 1 mg/ml in H$_2$O:MeOH=1:1, containing 2 mM ammonium acetate. A sample of 10 µl was injected into an HPLC instrument (Agilent 1100) using a Phenomenex Luna 3µ C18 column. Elution was performed with a gradient of water:methanol (containing 2 mM ammonium acetate) from 90:10 to 0:100 for 30 min at a flow rate of 250 µl/min, starting the gradient after 10 min. UV absorption was detected from 190-400 nm using a diode array detector.

General Procedure for the Synthesis of Nucleosides

Synthesis of 2-Thioadenosine

Adenosine was oxidized with hydrogen peroxide in acetic acid yielding the N1-oxide. Subsequent ring opening using sodium hydroxide followed by treatment with a mixture of carbon disulfide, methanol and water (50:175:25) at 120° C. in an autoclave gave 2-thioadenosine.

Synthesis of 2-Thioadenosine Derivatives

Alkylation of 2-thioadenosine with alkyl or arylalkyl halogenides was performed in the presence of sodium methoxide in DMF or NaOH in water, to yield 2-alkylthio-substituted adenosine derivatives.[2,3]

The new nucleoside 2-cyclohexylethylthioadenosine was synthesized from 2-thioadenosine through alkylation with cyclohexylethyl bromide in the presence of NaOH in water.

$^1$H-NMR (500 MHz, DMSO-d$_6$), 0.87-1.60 (m, 11H, cyclohexyl-CH$_2$—CH$_2$—S—R), 1.61-1.74 (m, 2H, cyclohexyl-CH$_2$—CH$_2$—S—R), 3.0-3.14 (m, 2H, cyclohexyl-CH$_2$—CH$_2$—S—R), 3.50-3.64 (m, 2H, C'5-H), 3.88-3.91 (q, 1H, J=3.99 Hz, C'4-H), 4.10-4.12 (t, 1H, J=4.25 Hz, C'3-H), 4.58-4.60 (t, 1H, J=5.35 Hz, C'2-H), 4.96-4.99 (t, 1H, J=5.51 Hz, C'S—OH), 5.10 (m, 1H, C'2—OH), 5.36 (m, 1H, C'3—OH), 5.80-5.81 (d, 1H, J=5.99 Hz, C'1-H), 7.28 (s, 2H, C'6—NH$_2$), 8.19 (s, 1H, C8-H).

$^{13}$C-NMR (125 MHz, DMSO-d$_6$), δ 25.89 (C3, C5 cyclohexyl), 26.26 (C4 cyclohexyl), 27.94 (cyclohexyl-CH$_2$—CH$_2$—S—R), 32.46 (C2, C6 cyclohexyl), 36.61 (cyclohexyl-CH$_2$—CH$_2$—S—R), 36.82 (C1 cyclohexyl), 61.75 (C'5), 70.60 (C'3), 73.31 (C'2), 85.57 (C'4), 87.42 (C'1), 117.05 (C5), 138.86 (C8), 150.31 (C4), 155.63 (C6), 163.94 (C2).

General Procedure for Phosphorylation

Preparation of Triethylammonium Hydrogen Carbonate Buffer (TEAB)

A 1 M solution of TEAB was prepared by bubbling CO$_2$ through a 1 M triethylamine solution in water at 0-4° C. for several hours (pH approx. 7.4-7.6).[4]

General Procedure for the Preparation of Monophosphates by Phosphorylation of Nucleosides (or Analogs)

Lyophilized nucleoside (1 mmol) was dissolved in 5 ml of trimethyl phosphate (dried over 10 Å molecular sieve). The mixture was stirred at rt under argon and then cooled to 4'C. Dry 1,8-bis(dimethylamino)naphthaline (proton sponge, 0.32 g, 1.5 mmol) was added, followed by 0.20 g (1.3 mmol) of POCl$_3$ 5 min later. After several hours of stirring at 0-4° C., the mixture was poured into a cold 0.5 M aqueous TEAB solution (10 ml, pH 7.5) and stirred at 0-4° C. for several minutes. The solution was allowed to reach room temperature upon stirring and then left standing for one hour. Trimethyl phosphate was extracted with tert.-butylmethyl ether and the aqueous solution was evaporated and lyophilized to yield glassy colorless oils. The reactions were controlled by TLC using a freshly prepared solvent system (2-propanol:NH$_4$OH:water=6:3:1). TLC plates were dried before UV absorption was detected and the plates were subsequently sprayed with a phosphate reagent.[4,5]

Purification of Monophosphates Using Preparative HPLC

Lyophilized nucleoside 5'-monophosphates were dissolved in 5 ml of deionized water and injected into an RP-HPLC column (Knauer 20 mm ID, Eurospher-100 C18). The column was eluted with a solvent gradient of 0-50% of acetonitrile in 50 mM aq. NH$_4$HCO$_3$ buffer for 40 min at a flow rate of 5 ml/min. The UV absorption was detected at 254 nm. Fractions were collected and appropriate fractions pooled, diluted with water and lyophilized several times to remove the NH$_4$HCO$_3$ buffer yielding the products as white powders.

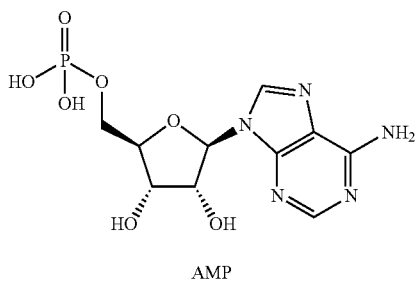

AMP

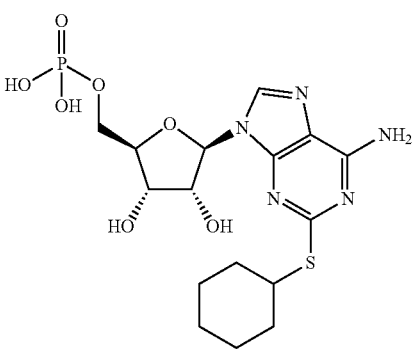 [SMILES: Nc1nc(SC2CCCCC2)nc2c1ncn2[C@@H]1O[C@H](COP(=O)(O)O)[C@@H](O)[C@H]1O]

1

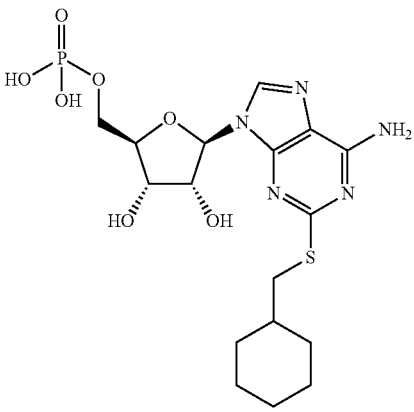 [SMILES: Nc1nc(SCC2CCCCC2)nc2c1ncn2[C@@H]1O[C@H](COP(=O)(O)O)[C@@H](O)[C@H]1O]

2

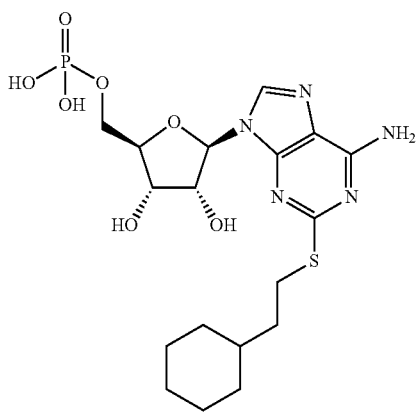 [SMILES: Nc1nc(SCCC2CCCCC2)nc2c1ncn2[C@@H]1O[C@H](COP(=O)(O)O)[C@@H](O)[C@H]1O]
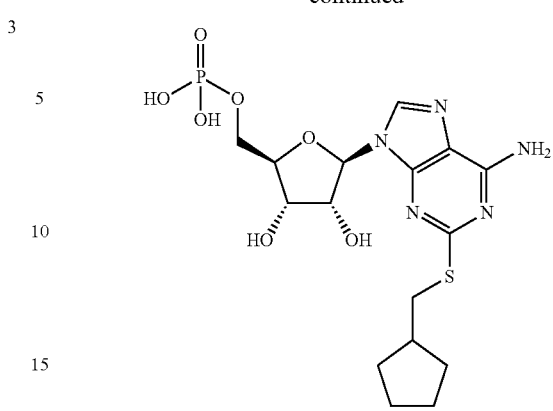
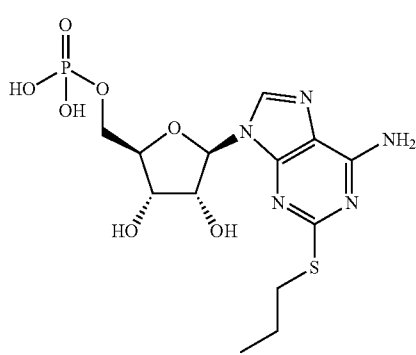 [SMILES: CCCSc1nc(N)c2ncn([C@@H]3O[C@H](COP(=O)(O)O)[C@@H](O)[C@H]3O)c2n1]
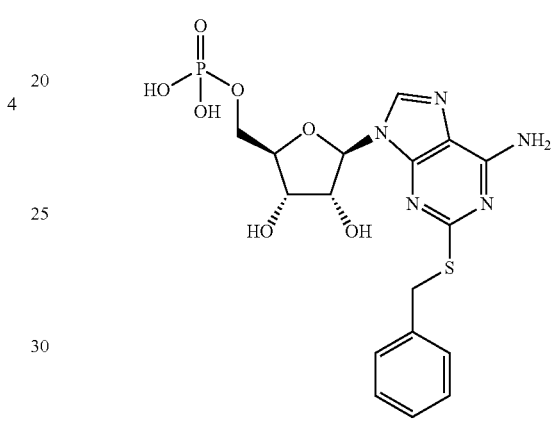
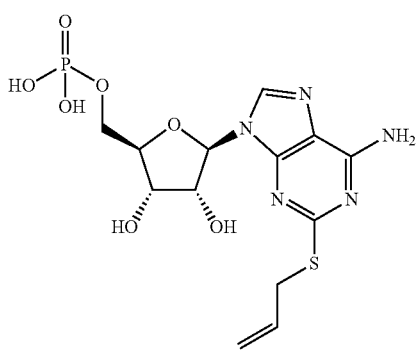 [SMILES: C=CCSc1nc(N)c2ncn([C@@H]3O[C@H](COP(=O)(O)O)[C@@H](O)[C@H]3O)c2n1]
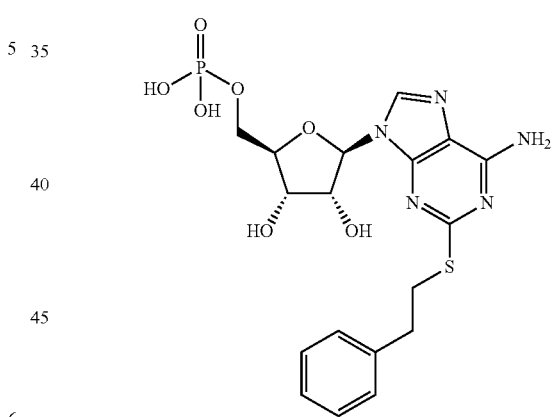
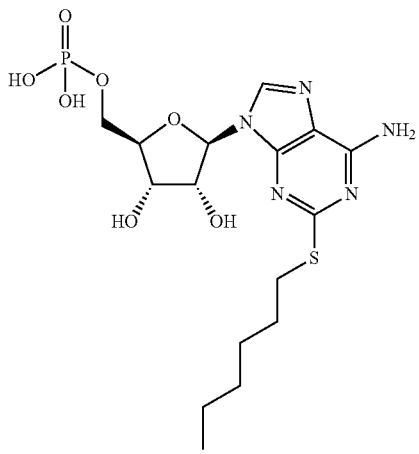 [SMILES: CCCCCCSc1nc(N)c2ncn([C@@H]3O[C@H](COP(=O)(O)O)[C@@H](O)[C@H]3O)c2n1]
FIG. 1. Examples of nucleoside 5'-monophosphates derivatives investigated as potential substrates of ecto-5'-nucleotidase (ecto-5'-NT).
Example No. 1
2-(Cyclohexylthio)adenosine-5'-monophosphate
$^1$H-NMR (500 MHz, D$_2$O), 1.46-2.07 (m, 11H, cyclohexyl-S—R), 4.06-4.10 (m, 2H, C'5-H), 4.24 (m, 1H, C'4-H), 4.34 (t, 1H, J=3.46 Hz, C'3-H), 4.50 (t, 1H, J=5.04 Hz, C2-H), 6.07-6.08 (d, 1H, J=5.35 Hz, C'1-H), 8.33 (s, 1H, C8-H).
$^{13}$C-NMR (125 MHz, D$_2$O), δ 28.11 (C3, C5 cyclohexyl), 28.44 (C4 cyclohexyl), 35.44 (C2, C6 cyclohexyl), 47.17

(C1 cyclohexyl), 67.20 (C'5), 73.32 (C'3), 76.67 (C'2), 86.69 (C'4), 90.30 (C'1), 119.35 (C5), 142.42 (C8), 153.06 (C4), 158.22 (C6), 167.77 (C2).

$^{31}$P-NMR (202 MHz, D$_2$O), δ (ppm) 0.63 (s).
MS (ESI)
m/z+1: 462
m/z−1: 460

Example No. 2

2-(Cyclohexylmethylthio)adenosine-5'-monophosphate $^1$H-NMR (500 MHz, D$_2$O+NaOD), 1.0-1.82 (m, 11H, cyclohexyl-CH$_2$—S—R), 2.24 (s, 2H, cyclohexyl-CH$_2$—S—R), 3.88-3.98 (m, 2H, C'5-H), 4.19-4.23 (m, 2H, C'4-H and C'3-H), 4.67-4.68 (t, 1H, J=5.51 Hz, C'2-H), 5.88-5.89 (d, 1H, J=5.67 Hz, C'1-H), 8.36 (s, 1H, C8-H).

$^{13}$C-NMR (125 MHz, D$_2$O+NaOD), δ 28.49 (C3, C5 cyclohexyl), 28.76 (C4 cyclohexyl), 34.94 (C2, C6 cyclohexyl), 35.05 (C1 cyclohexyl), 40.38 (cyclohexyl-CH$_2$—CH$_2$—S—R), 67.24 (C'5), 74.65 (C'3), 78.63 (C'2), 87.94 (C'4), 91.14 (C'1), 119.27 (C5), 142.55 (C8), 153.40 (C4), 156.17 (C6), 168.48 (C2).

$^{31}$P-NMR (202 MHz, D$_2$O+NaOD), δ (PPrn) 4.79 (s).
MS (ESI)
m/z+1: 476
m/z−1: 474

Example No. 3

2-(Cyclohexylethylthio)adenosine-5'-monophosphate $^1$H-NMR (500 MHz, D$_2$O), 0.92-1.67 (m, 11H, cyclohexyl-CH$_2$—CH$_2$—S—R), 1.73-1.75 (m, 2H, cyclohexyl-CH$_2$—CH$_2$—S—R), 3.28-3.36 (m, 2H, cyclohexyl-CH$_2$—CH$_2$—S—R), 3.99 (m, 2H, C'5-H), 4.33-434 (m, 1H, C'4-H), 4.50 (m, 1, C'3-1), 4.70 (m, 1H, C'2-H), 6.10-6.11 (d, 1H, J=5.67 Hz, C'1H), 8.45 (s, 1H, C8-H).

$^{13}$C-NMR (125 MHz, D$_2$O), δ 27.71 (C3, C5 cyclohexyl), 28.02 (C4 cyclohexyl), 29.86 (cyclohexyl-CH$_2$—CH$_2$—S—R), 34.65 (C2, C6 cyclohexyl), 38.61 (cyclohexyl-CH$_2$—CH$_2$—S—R), 38.70 (C1 cyclohexyl), 66.16 (C'5), 72.75 (C'3), 76.49 (C'2), 86.18 (C'4), 88.85 (C'1), 117.05 (C5), 140.15 (C8), 150.25 (C4), 156.91 (C6), 168.44 (C2).

$^{31}$P-NMR (202 MHz, D$_2$O), δ (ppm) 0.51 (s).
MS (ESI)
m/z+1: 490
m/z−1: 488

Example No. 4

2-(Propylthio)adenosine-5'-monophosphate $^1$H-NMR (500 MHz, D$_2$O), δ (ppm) 0.96-0.99 (t, 3H, J=7.40 Hz, CH$_3$—CH$_2$—CH$_2$—S—R), 1.68-1.73 (m, 2H, CH$_3$—CH$_2$—CH$_2$—S—R), 3.14-3.18 (m, 2H, CH$_3$—CH$_{2-2}$—S—R), 4.04 (m, 2H, C'5-H), 4.30 (m, 1H, C'4-H), 4.46 (m, 1H, C'3-H), 4.57-4.59 (m, 1H, C'2-H), 6.05-6.06 (d, 1H, J=5.35 Hz, C'1-H), 8.32 (s, 1H, C8-H).

$^{13}$C-NMR (125 MHz, D$_2$O), δ (ppm) 15.48 (CH$_3$—CH$_2$—CH$_2$—S—R), 25.18 (CH$_3$—CH$_2$—CH$_2$—S—R), 35.74 (CH$_3$—CH$_2$—CH$_2$—S—R), 67.09 (C'5), 73.35 (C'3), 76.80 (C'2), 86.02 (C'4), 90.02 (C'1), 117.12 (C5), 141.99 (C8), 150.25 (C4), 158.02 (C6), 168.44 (C2).

$^{31}$P-NMR (202 MHz, D$_2$O), δ (ppm) 1.72 (s).
MS (ESI):
m/z+1: 422
m/z−1: 420

Example No. 5

2-(Allylthio)adenosine-5'-monophosphate $^1$H-NMR (500 MHz, D$_2$O+NaOD), δ (ppm) 3.65-3.72 (m, 2H, CH$_2$=CH—CH$_2$S—R), 3.74-3.87 (m, 2H, C'5-H), 4.05-4.08 (m, 2H, C'4-H and C'3-H), 4.50-4.52 (t, 1H, J=5.20 Hz, C'2-H), 5.01-5.03 (d, 1H, J=10.08 Hz, CH$_2$=CH—CH$_2$—S—R), 5.20-5.24 (m, 1H, CH$_2$=CH—CH$_2$—S—R), 5.74-5.75 (d, 1H, J=5.35 Hz, C'1-H), 5.86-5.94 (m, 1H, CH$_2$=CH—CH$_2$—S—R), 8.22 (s, 1H, C8-H).

$^{13}$C-NMR (125 MHz, D$_2$O+NaOD), δ (ppm) 36.49 (CH$_2$=CH—CH$_2$—S—R), 65.54 (C'5), 74.69 (C'3), 78.80 (C'2), 87.69 (C'4), 91.50 (C'1), 119.35 (CH$_2$=CH—CH$_2$—S—R), 120.67 (C5), 136.90 (CH$_2$=CH—CH$_2$—S—R), 143.52 (C8), 153.22 (C4), 162.0 (C6), 167.07 (C2).

$^{31}$P-NMR (202 MHz, D$_2$O+NaOD), δ (ppm) 5.87 (s).
MS (ESI):
m/z+1: 420
m/z−1: 418

Example No. 6

2-(Hexylthio)adenosine-5'-monophosphate $^1$H-NMR (500 MHz, D$_2$O), 0.78 (t, 3H, J=6.30 Hz, C''6-H), 1.19-1.62 (m, 8H, C''5-H to C''2-H), 3.11-3.13 (m, 2H, C''1-H), 4.02 (m, 3H, C'5-H and C'4-H), 4.25 (m, 1H, C'3-H), 4.40-4.41 (t, 1H, J=4.25 Hz, C'2-H), 5.98-5.99 (d, 1H, J=5.35 Hz, C'1-H), 8.20 (s, 1H, C8-H).

$^{13}$C-NMR (125 MHz, MeOD), δ 14.68 (C''6-H), 23.95 (C''5-H), 29.96 (C''3-H), 30.92 (C''2-H), 32.21 (C''4-H), 32.93 (C''1-H), 66.23 (C'5), 72.72 (C'3), 76.45 (C'2), 86.09 (C'4), 88.99 (C'1), 123.0 (C5), 140.17 (C8), 152.32 (C4), 156.92 (C6), 167.33 (C2).

$^{31}$P-NMR (202 MHz, D$_2$O), δ (ppm) 0.35 (s).
MS (ESI)
m/z+1: 464
m/z−1: 462

Example No. 7

2-(Cyclopentylmethylthio)adenosine-5'-monophosphate $^1$H-NMR (500 MHz, D$_2$O+NaOD), 1.31-2.11 (m, 9H, cyclopentyl-CH$_2$—S—R), 2.83 (s, 2H, cyclopentyl-CH$_2$—S—R), 3.85-3.92 (m, 3H, C'4-H and C'5-H), 4.23 (in, 1H, C'3-1), 4.39 (m, 1H, C'2-H), 5.98-5.99 (d, 1H, J=5.67 Hz, C'1-H), 8.30 (s, 1H, C8-H).

$^{13}$C-NMR (125 MHz, D$_2$O+NaOD), δ 27.47 (C3, C4 cyclopentyl), 35.99 (C2, C5 cyclopentyl), 47.18 (C1-cyclopentyl), 48.75 (cyclopentyl-CH$_2$—S—R), 58.79 (C'5), 73.66 (C'3), 77.12 (C'2), 87.28 (C'4), 90.32 (C'1), 120.32 (C5), 142.57 (C8), 150.18 (C4), 158.31 (C6), 163.70 (C2).

$^{31}$P-NMR (202 MHz, D$_2$O+NaOD), δ (ppm) 2.68 (s).
MS (ESI)
m/z+1: 448
m/z−1: 446

Example No. 8

2-(Benzylthio)adenosine-5'-monophosphate $^1$H-NMR (500 MHz, MeOD), δ 3.52-3.76 (m, 2H, phenyl-CH$_2$—S—R), 4.0-4.11 (m, 2H, C'5-H), 4.22-4.25 (q, 1H, J=4.09 Hz, C'4-H), 4.32-4.34 (q, 1H, J=4.88 Hz, C'3-H), 4.64-4.66 (t, 1H, J=5.04 Hz, C'2-H), 6.03-6.04 (d, 1H, J=4.72 Hz, C'1-H), 7.25-7.50 (m, 5H, aromatic), 8.48 (s, 1H, C8-H).

$^{31}$P-NMR (202 MHz, MeOD), δ 2.53 (s).

MS (ESI):

m/z+1: 470 m/z−1: 468

Example No. 9

2-(Phenylethylthio)adenosine-5'-monophosphate $^{1}$H-NMR (500 MHz, MeOD), δ 3.05-3.08 (t, 2H, J=7.72 Hz, phenyl-CH$_2$—CH$_2$—S—R), 3.38-3.49 (m, 2H, phenyl-CH$_2$—CH$_2$—S—R), 3.76-3.90 (m, 2H, C'5-1-1), 4.16-4.18 (q, 1H, J=3.25 Hz, C'4-H), 3.34-3.35 (q, 1H, J=4.34 Hz, C'3-H), 4.74-4.76 (t, 1H, J=4.75 Hz, C'2-H), 6.02-6.03 (d, 1H, J=5.67 Hz, C'1-H), 7.20-7.36 (m, 5H, aromatic), 8.24 (s, 1H, C8-H).

$^{13}$C-NMR (125 MHz, MeOD), δ 33.84 (phenyl-CH$_2$—CH$_2$—S—R), 37.52 (phenyl-CH$_2$—CH$_2$—S—R), 63.51 (C'5), 72.58 (C3), 75.70 (C2), 87.72 (C4), 90.65 (C'1), 123.02 (C5), 127.56-130.88 (6C, aromatic) 140.77 (C8), 150.25 (C4), 157.19 (C6), 166.92 (C2).

$^{31}$P-NMR (202 M Hz, MeOD), δ 0.54 (s).

MS (ESI):

m/z+1: 484 m/z−1: 482

Example No. 10

2-Propargylthioadenosine-5'-monophosphate m/z+1: 418 m/z−1: 418

Ecto-5'-Nucleotidase Assays by Capillary Electrophoresis (CE)

Materials and Methods

Reagents and Chemicals

Adenosine, MgCl$_2$.6H$_2$O, sucrose, dimethyl sulfoxide (DMSO), and AMP were from Sigma (Taufkirchen, Germany). 4-(2-Hydroxyethyl)piperazine-1-ethanesulfonic acid (HEPES) was obtained from Sigma-Aldrich, Steinheim, Germany.

Recombinant Expression of Rat Ecto-5'-Nucleotidase

Catalytically active recombinant soluble glutathione-S-transferase/ecto-5'-nucleotidase fusion protein (rat enzyme) was expressed in insect cells using the baculovirus system and purified by affinity chromatography using agarose-coupled GSH as previously described.[6] The enzyme was obtained from Prof. Dr. Herbert Zimmermann, University of Frankfurt.

Capillary Electrophoresis Methods

Preparation of Standard Solutions

Compounds were dissolved in DMSO to obtain 5.0 mM stock solutions. These were further diluted to obtain 1 mM solutions in assay buffer (10 mM Hepes, pH 7.4, 2 mM MgCl$_2$, 1 mM CaCl$_2$). The 1 mM solutions were further diluted in the same buffer as required for the standard calibration curves and the enzyme assays.

Capillary Enzymatic Reaction

CE separations were carried out using a P/ACE MDQ system (Beckman Coulter Instruments, Fullerton, Calif., USA) equipped with a DAD detection system. The electrophoretic separations were carried out using an eCAP fused-silica capillary [30 cm (20 cm effective length), ×75 μm internal diameter (I.D), ×375 μm outside diameter (O.D) obtained from Beckman Coulter]. The following conditions were applied: T=25° C., λ$_{max}$=232 nm, voltage=15 kV, running buffer 40 mM sodium borate buffer, pH 9.1. The capillary was washed with 0.1 M NaOH for 2 min, deionized water for 1 min, and running buffer for 1 min before each injection. Injections were made by applying 0.1 psi of pressure to the sample solution for 30 s. The amount of adenosine or other nucleosides formed was determined. The CE instrument was fully controlled through a personal computer, which operated with the analysis software 32 KARAT obtained from Beckman Coulter. Electropherograms were evaluated using the same software.

Investigation of Ecto-5'-Nucleotidase Substrates by Capillary Electrophoresis

Ecto-5'-nucleotidase substrate specificity assays were performed by using capillary electrophoresis method. Enzyme substrate assays were carried out at 37° C. in a final volume of 100 μl. The reaction mixture contained 500 μM of the nucleoside 5'-monophosphate to be investigated dissolved in reaction buffer (10 mM Hepes, pH 7.4, 2 mM MgCl$_2$, 1 mM CaCl$_2$). The reactions were initiated by adding 10 μl of the appropriately diluted enzyme and was then allowed to proceed at 37° C. for 20 min. The reaction was stopped by heating the mixture at 99° C. for 5 min. Aliquots of 50 μl of the reaction mixture were transferred to mini CE vials and injected into the CE instrument under the conditions described above. The absorbance at 232 nm was monitored continuously and the nucleoside concentrations were determined from the area under each absorbance peak. The experiments were repeated twice with triplicate injections. Control experiments were performed in the absence of substrate and in the absence of enzyme in order to take into account the spontaneous hydrolysis of nucleoside-5' monophosphates under the experimental conditions, which always amounted to less than 1%.

All of the nucleosides were injected into the capillary electrophoresis under the same assay conditions at 500 μM concentrations to confirm the migration times of the nucleoside peaks observed after enzymatic hydrolysis of the nucleoside monophosphates.

For the quantification of the dephosphorylation reaction products, we applied the internal normalization method. Thus, the individual peak areas reflected directly the relative content of a corresponding analyte. This was possible since educt (nucleoside monophosphate) and product (nucleoside) exhibit the same molar absorption coefficient; the phosphate residue does not show any UV absorption at the wavelength used for quantification (232 nm). It was verified that in fact there were no observable differences in detector response at the used wavelength and thus no additional correction factors had to be employed for the calculation of the amount of product relative to the amount of substrate. This method is also completely independent of the amount of substrate injected into the capillary which represents 100% at zero reaction time.

Investigation of Alternative Substrates Using CE

Besides AMP, other nucleoside 5'-monophosphates (FIG. 1) were investigated as alternative substrates of ecto-5'-NT. All nucleotides (AMP) were used at a concentration of 500 μM in the presence of 2 mM MgCl$_2$, 1 mM CaCl$_2$, 10 mM Hepes, pH, 7.4, and suitably diluted ecto-5'-NT. Some of the nucleoside 5'-monophosphates were efficiently dephosphorylated to the corresponding nucleosides by the enzyme (Table 1).

The best substrate of the present series of 9-substituted nucleoside 5'-monophosphates derivatives was compound 3, exhibiting 95% of dephosphorylation in comparison with AMP (set at 100%).

TABLE 1

Percent dephosphorylation of adehosine 5'-monophosphates derivativesby-ecto-5'-nucleotidase in comparison with the physiological substrate AMP

| Compound No. | Compound | Dephosphorylation (%)$^a$ (n = 3) |
|---|---|---|
| AMP | [structure] | 100 ± 1.15 |
| 1 | [structure] | 27.5 ± 1.45 |
| 2 | [structure] | 70.5 ± 1.17 |

TABLE 1-continued

Percent dephosphorylation of adehosine 5'-monophosphates derivativesby-ecto-5'-nucleotidase in comparison with the physiological substrate AMP

| Compound No. | Compound | Dephosphorylation (%)$^a$ (n = 3) |
|---|---|---|
| 3 | [structure] | 95.7 ± 1.15 |
| 4 | [structure] | 46.8 ± 10.5 |
| 5 | [structure] | 0 |

TABLE 1-continued

Percent dephosphorylation of adehosine 5'-monophosphates derivativesby-ecto-5'-nucleotidase in comparison with the physiological substrate AMP

| Compound No. | Compound | Dephosphorylation (%)a (n = 3) |
|---|---|---|
| 6 | 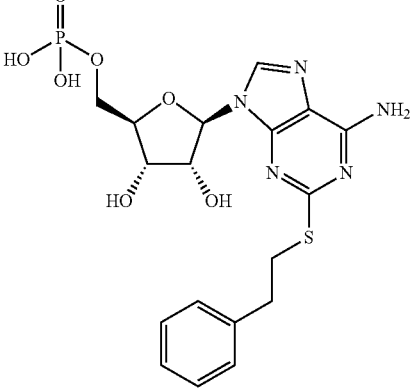 | 84.2 ± 2.61 |
| 7 | 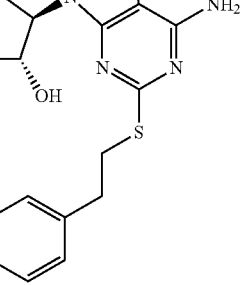 | n.d. |
| 8 | 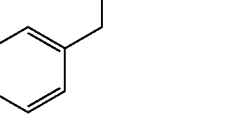 | 0 |

TABLE 1-continued

Percent dephosphorylation of adehosine 5'-monophosphates derivativesby-ecto-5'-nucleotidase in comparison with the physiological substrate AMP

| Compound No. | Compound | Dephosphorylation (%)a (n = 3) |
|---|---|---|
| 9 | 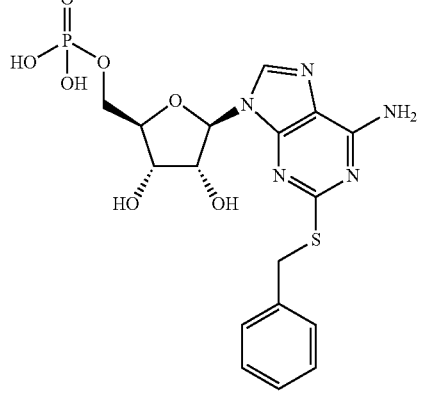 | 0 | aPercentage of dephosphorylation of nucleoside monophosphates was calculated with respect to the dephosphorylation of AMP, set at 100%. The peak areas of the substrate peak (nucleoside monophosphate) and the product peak (nucleoside) were measured and quantified in the same electropherogram. The amount of nucleosides formed were related to the amount of adenosine formed by dephosphorylation of AMP.

Determination of Adenosine Receptor Affinities of Nucleosides

Chemicals

Tris was obtained from Acros Organics (Leverkusen, Germany); DMSO was from Fluka (Switzerland), HCl was from Merck, HAT supplement from Gibco. [$^3$H]CCPA ([$^3$H]2-chloro-N$^6$-cyclopentyladenosine), [$^3$H]MSX-2 ([$^3$H]3-(3-hydroxypropyl)-7-methyl-8-(m-methoxy-styryl)-1-propargylxanthine) (84 Ci/mmol), and [$^3$H]DSB-11 ([$^3$H]8-ethyl-4-methyl-2-phenyl-(8R)-4,5,7,8-tetrahydro-1H-imidazo[2,1-i]-purin-5-one (53 Ci/mmol)) were custom-labeled by Amersham. All other chemical reagents, cell culture materials and adenosine receptor ligands were obtained from Sigma.

Receptor-Radioligand Binding Studies

Radioligand binding studies were performed as previously described.[7,8]

TABLE 2

Adenosine receptor affinities of nucleosides (dephosphorylated products)

| Nucleoside formed from nucleotide No. (2-substituent) | $A_1$ receptor rat brain cortical membranes vs. [$^3$H]CCPA$^a$ $K_i$ [nM] | $A_{2A}$ receptor rat brain striatal membranes vs. [$^3$H]MSX-2$^b$ $K_i$ [nM]$^c$ | $A_3$ receptor human recombinant receptors expressed in CHO cells vs. [$^3$H]PSB-11$^b$ $K_i$ [nM]$^c$ |
|---|---|---|---|
| 2 (cyclohexylmethylthio) | 498 | 4000 | 1700 |
| 3 (cyclohexylmethylthio) | 400 | 50 | 3600 |
| 4 (propylthio) | 1270 | 1350 ([$^3$H]CGS21680)$^a$ | n.d. |
| 6 (hexylthio) | 256 | 1000 | 2300 |
| 7 (cyclopentylmethylthio) | n.d. | 7600 | n.d. |
| 8 (benzylthio) | 927 | 8560 | 120 |
| 9 (phenethylthio) | 180 | 60 | 1200 |
| 10 (cyclopentylthio) | 994 | n.d. | 10400 |
| 11 (propargylthio) | 555 | 14200 | 6900 |
| 12 (—S—CH$_2$—COOH) | 1930 | >10000 | >10000 |

$^a$Agonist radioligand
$^b$Antagonist radioligand
$^c$Affinities of the agonists will be underestimated since an antagonist radioligand was used for the determination.

REFERENCES

1. Kikugawa, K.; Suehiro, H.; Yanase, R. Platelet aggregation inhibitors IX. Chemical transformation of adenosine into 2-thioadenosine derivatives. *Chem. Pharm. Bull.* 1977, 25, 1959-1969.
2. Ingall, A. H.; Dixon, J.; Bailey, A.; Coombs, M. E.; Cox, D.; McInally, I. J.; Hunt, S. F.; Kindon, N. D.; Teobald, B. J.; Willis, P. A.; Humphries, R. G.; Leff, P.; Clegg, J. A.; Smith, J. A.; Tomlinson, W. Antagonists of the platelet P2T receptor: a novel approach to antithrombotic therapy. *J. Med. Chem.* 1999, 42, 213-220.
3. Kikugawa, K.; Suehiro, H.; Aoki, A. Platelet aggregation inhibitors. X. S-Substituted 2-thioadenosines and their derivatives. *Chem. Pharm. Bull.* 1977, 25, 2624-2637.
4. Knoblauch, B. H. A.; Muller, C. E.; Järlebark, L.; Lawoko, G.; Kottke, T.; Wikström, M. A.; Heilbronn, E. 5-Substituted UTP derivatives as P2Y$_2$ receptor agonists. *Eur. J Med. Chem.* 1999, 34, 809-824.
5. Ludwig, J. A new route to nucleoside 5'-triphosphates. *Acta Biochim. Biophys. Acad. Sci. Hung.* 1981, 16, 131-133.
6. Servos, J.; Reilander, H.; Zimmermann, H. *Drug Dev. Res.* 1998, 45, 269-276.
7. Yan, L.; Müller, C. E. Preparation, properties, reactions, and adenosine receptor affinities of sulfophenylxanthine nitrophenyl esters: Toward the development of sulfonic acid prodrugs with peroral bioavailability. *J. Med. Chem.* 2004, 47, 1031-1043.
8. Bulicz, J.; Bertarelli, D. C. G.; Baumert, D.; Fülle, F.; Müller, C. E.; Heber, D. Synthesis and pharmacology of pyrido[2,3-d]pyrimidinediones bearing polar substituents as adenosine receptor antagonists. *Bioorg. Med. Chem.* 2006, 14, 2837-2849.

The invention claimed is:

1. A method for treatment of a disease caused by an acute or chronic inflammatory, hypotensive, psychotic, or asthmatic event, comprising administering to a patient in need thereof a monophosphorylated $A_{2A}$ receptor agonist of formula (I)

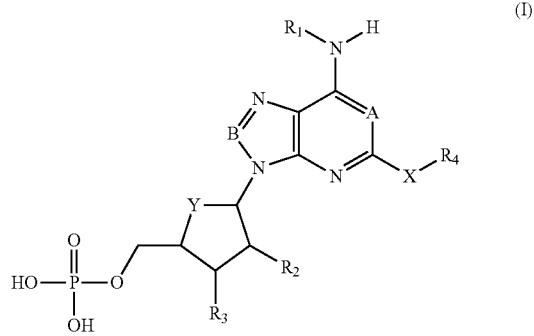

wherein:
A is CH;
B is CH or N;
Y is selected from the group consisting of NH, O, S, C=O, and $CH_2$;
$R^1$ is hydrogen, ($C_1$-$C_5$) alkyl, alkenyl or alkoxy;
X is selected from the group consisting of O, S, NH, C=O, C=S, $O(CH_2)_{1-3}$, $N(CH_2)_{1-3}$, $NH(CH_2)_{1-3}$, $S(CH_2)_{1-3}$, NHN=N, NHN=$NCH_2$, C(O)—$(CH_2)_{1-3}$, C(S)—$(CH_2)_{1-3}$, C=N=N, C≡C, C≡C—$(CH_2)_{1-3}$;
$R^2$, $R^3$ are, independently from each other, $OR^5$, $NR^5R^6$, $SR^5$, wherein $R^5$ and $R^6$ are, independently, hydrogen, lower alkyl such as Me, Et, nProp, iProp, nBu, sekBu, tertBu, alkoxy, alkylamino, $C_1$-$C_3$ alkylthio;
$R^4$ is selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, an unsubstituted or substituted 5- to 10-membered heteroalicyclic ring,
wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR',
wherein R and R' are independently of each other selected from the group
consisting of ($C_1$-$C_4$) alkyl and ($C_1$-$C_4$) alkenyl residues,
or a physiologically acceptable salt thereof.

2. The method of claim 1, wherein the inflammatory event is selected from the group consisting of arteriosclerosis, arthritis, Crohn's disease, traumatic spinal cord injury, restenosis of arteries, and a combination thereof.

3. The method of claim 1, wherein the inflammatory event is caused by an immune response to transplanted tissue.

4. The method of claim 3, wherein immune response is a transplant rejection, or graft versus host disease.

5. The method of claim 4, wherein immune response is a transplant rejection.

6. The method of claim 3, wherein the transplantation comprises an organ, tissue or cell transplantation.

7. The method of claim 6, wherein the cells are bone marrow, skin, or pancreatic islets.

8. The method of claim 7, wherein the cells are pancreatic islets.

9. The method of claim 6, wherein the organ is a cornea, kidney, lung, liver, or heart.

10. The method of claim 1, wherein the physiologically acceptable salt is selected from the group consisting of a sodium, potassium, ammonium, triethylammonium, and trimethylammonium salt.

11. A method for treatment of a disease caused by an acute or chronic inflammatory, hypotensive, phsycotic, or asthmatic event, comprising administering to a patient in need thereof a phosphorylated $A_{2A}$ receptor agonist of formula (I)

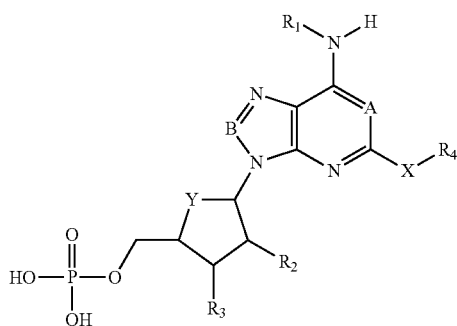

wherein
A and B are CH;
Y is O;
$R^1$ is selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl,
wherein 1 to 4 ring atoms are independently selected from nitrogen, oxygen or sulfur,
an unsubstituted or substituted 5- to 10-membered heteroalicyclic ring,
wherein 1 to 3 ring atoms are independently nitrogen, oxygen or sulfur, —OR, —C(O)R, —C(O)OR, —C(O)NRR', —NRR', —S(O)$_2$R, —S(O)$_2$OR,
wherein R and R' are independently of each other selected from the group consisting of ($C_1$-$C_4$) alkyl or ($C_1$-$C_4$) alkenyl residues;
X is selected from the group consisting of O, S, NH, C=O, C=S, O(CH$_2$)$_{1-3}$, N(CH$_2$)$_{1-3}$, NH(CH$_2$)$_{1-3}$, S(CH$_2$)$_{1-3}$, NHN=N, NHN=NCH$_2$, C(O)—(CH$_2$)$_{1-3}$, C(S)—(CH$_2$)$_{1-3}$, C=N=N, C≡C, C=C—(CH$_2$)$_{1-3}$;
$R^2$, $R^3$ are, independently from each other, OR$^5$, NR$^5$R$^6$, SR$^5$,
wherein R$^5$ and R$^6$ are, independently, hydrogen or lower alkyl chosen from Me, Et, nProp, iProp, nBu, sekBu, tertBu;
$R^4$ is selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl,
wherein 1 to 4 ring atoms are independently selected from nitrogen, oxygen or sulfur,
an unsubstituted or substituted 5- to 10-membered heteroalicyclic ring,
wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR',
wherein R and R' are, independently of each other, selected from the group consisting of ($C_1$-$C_4$) alkyl or ($C_1$-$C_4$) alkenyl residues,
or a physiologically acceptable salt thereof.

12. The method of claim 11, wherein the physiologically acceptable salt is selected from the group consisting of a sodium, potassium, ammonium, triethylammonium, and trimethylammonium salt.

13. The method of claim 11, wherein X is S.

14. A method for treatment of a disease caused by an acute or chronic inflammatory, hypotensive, phsychotic, or asthmatic event, comprising administering to a patient in need thereof a phosphorylated $A_{2A}$ receptor agonist selected from the group consisting of
2-(Cyclohexylthio)adenosine-5'-monophosphate;
2-(Cyclohexylmethylthio)adenosine-5'-monophosphate;
2-(Cyclohexylethylthio)adenosine-5'-monophosphate;
2-(Allylthio)adenosine-5'-monophosphate;
2-(Cyclopentylmethylthio)adenosine-5'-monophosphate; and
2-(Phenylethylthio)adenosine-5'-monophosphate.

15. The method of claim 11, wherein the inflammatory event is selected from the group consisting of arteriosclerosis, arthritis, Crohn's disease, traumatic spinal cord injury, restenosis of arteries, transplant rejection, graft versus host disease and a combination thereof.

16. A method for treatment of a disease caused by an acute or chronic inflammatory, hypotensive, psychotic, or asthmatic event, comprising administering to a patient in need thereof a monophosphorylated $A_{2A}$ receptor agonist of formula (I)

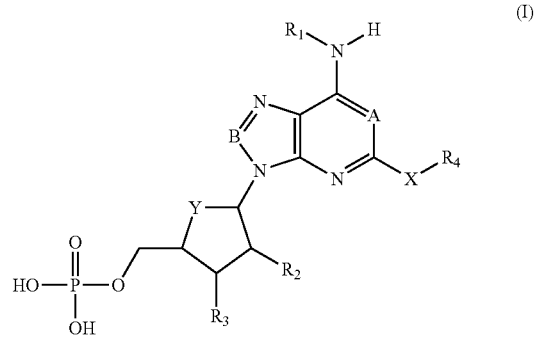

wherein:
A and B are, independently of each other, CH or N;
Y is selected from the group consisting of NH, O, S, C=O, and CH$_2$;
$R^1$ is hydrogen, ($C_1$-$C_5$) alkyl, alkenyl or alkoxy;
X is selected from the group consisting of O, NH, C=O, C=S, O(CH$_2$)$_{1-3}$, N(CH$_2$)$_{1-3}$, NH(CH$_2$)$_{1-3}$, NHN=N, NHN=NCH$_2$, C(O)—(CH$_2$)$_{1-3}$, C(S)—(CH$_2$)$_{1-3}$, C=N=N, C≡C, C=C—(CH$_2$)$_{1-3}$;
$R^2$, $R^3$ are, independently from each other, OR$^5$, NR$^5$R$^6$, SR$^5$, wherein R$^5$ and R$^6$ are, independently, hydrogen, lower alkyl such as Me, Et, nProp, iProp, nBu, sekBu, tertBu, alkoxy, alkylamino, $C_1$-$C_3$ alkylthio;
$R^4$ is selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, an unsubstituted or substituted 5- to 10-membered heteroalicyclic ring,
wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR',
wherein R and R' are independently of each other selected from the group consisting of ($C_1$-$C_4$) alkyl and ($C_1$-$C_4$) alkenyl residues,
or a physiologically acceptable salt thereof.

17. The method of claim 16, wherein the inflammatory event is selected from the group consisting of arteriosclerosis, arthritis, Crohn's disease, traumatic spinal cord injury, restenosis of arteries, transplant rejection, graft versus host disease and a combination thereof.

18. The method of claim 16, wherein the physiologically acceptable salt is selected from the group consisting of a sodium, potassium, ammonium, triethylammonium, and trimethylammonium salt.

19. A method for treatment of a disease caused by an acute or chronic inflammatory, hypotensive, psychotic, or asthmatic event, comprising administering to a patient in need thereof a monophosphorylated $A_{2A}$ receptor agonist of formula (I)

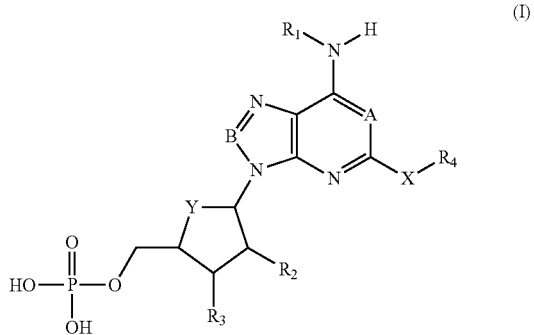

wherein:

A and B are, independently of each other, CH or N;

Y is selected from the group consisting of NH, O, S, C=O, and $CH_2$;

$R^1$ is hydrogen, $(C_1\text{-}C_5)$ alkyl, alkenyl or alkoxy;

X is selected from the group consisting of O, S, NH, C=O, C=S, $O(CH_2)_{1-3}$, $N(CH_2)_{1-3}$, $NH(CH_2)_{1-3}$, $S(CH_2)_{1-3}$, NHN=N, NHN=$NCH_2$, C(O)—$(CH_2)_{1-3}$, C(S)—$(CH_2)_{1-3}$, C=N=N, C≡C, C≡C—$(CH_2)_{1-3}$;

$R^2$, $R^3$ are, independently from each other, $OR^5$, $NR^5R^6$, $SR^5$, wherein $R^5$ and $R^6$ are, independently, hydrogen, lower alkyl such as Me, Et, nProp, iProp, nBu, sekBu, tertBu, alkoxy, alkylamino, $C_1\text{-}C_3$ alkylthio;

$R^4$ is selected from the group consisting of hydrogen, unsubstituted or substituted $C_1\text{-}C_{10}$ alkenyl, unsubstituted or substituted $C_1\text{-}C_{10}$ alkynyl, unsubstituted or substituted $C_3\text{-}C_8$ cycloalkyl, unsubstituted or substituted $C_1\text{-}C_{10}$ alkoxy, unsubstituted or substituted $C_3\text{-}C_8$ cycloalkoxy, an unsubstituted or substituted 5-to 10-membered heteroalicyclic ring, wherein 1 to 3 ring atoms are independently nitrogen, oxygen or sulfur, —OR, —C(O)R, —C(O)OR, —C(O)NRR', —NRR', —S(O)$_2$R, —S(O)$_2$OR, and —S(O)$_2$NRR', wherein R and R' are independently of each other selected from the group consisting of $(C_1\text{-}C_4)$ alkyl and $(C_1\text{-}C_4)$alkenyl residues, or a physiologically acceptable salt thereof.

20. The method of claim 19, wherein the inflammatory event is selected from the group consisting of arteriosclerosis, arthritis, Crohn's disease, traumatic spinal cord injury, restenosis of arteries, transplant rejection, graft versus host disease and a combination thereof.

21. The method of claim 19, wherein the physiologically acceptable salt is selected from the group consisting of a sodium, potassium, ammonium, triethylammonium, and trimethylammonium salt.

* * * * *